US009983142B2

(12) United States Patent
Acheson et al.

(10) Patent No.: US 9,983,142 B2
(45) Date of Patent: May 29, 2018

(54) REAPING BASED YIELD MONITORING SYSTEM AND METHOD FOR THE SAME

(71) Applicant: Raven Industries, Inc., Sioux Falls, SD (US)

(72) Inventors: John Earl Acheson, Sioux Falls, SD (US); Jared Ernest Kocer, Sioux Falls, SD (US)

(73) Assignee: Raven Industries, Inc., Sioux Falls, SD (US)

( * ) Notice: Subject to any disclaimer, the term of this patent is extended or adjusted under 35 U.S.C. 154(b) by 0 days. days.

(21) Appl. No.: 14/687,692

(22) Filed: Apr. 15, 2015

(65) Prior Publication Data

US 2015/0293029 A1 Oct. 15, 2015
US 2017/0038304 A9 Feb. 9, 2017

Related U.S. Application Data

(63) Continuation of application No. PCT/US2015/025801, filed on Apr. 14, 2015.
(Continued)

(51) Int. Cl.
*G01N 21/84* (2006.01)
*G01N 33/00* (2006.01)
*A01D 41/127* (2006.01)

(52) U.S. Cl.
CPC ........... *G01N 21/84* (2013.01); *A01D 41/127* (2013.01); *G01N 33/0098* (2013.01); *G01N 2021/8466* (2013.01)

(58) Field of Classification Search
CPC . A01D 41/127; A01D 41/1271; A01F 12/181; A01F 12/28; A01G 33/0098; A01G 21/84; A01G 2021/8466
See application file for complete search history.

(56) References Cited

U.S. PATENT DOCUMENTS 4,883,964 A 11/1989 Bohman
5,635,911 A 6/1997 Landers et al.
(Continued)

FOREIGN PATENT DOCUMENTS

AU 2009/203195 A1 5/2010
AU 2008/261611 B2 9/2013
(Continued)

OTHER PUBLICATIONS

"International Application Serial No. PCT/US2015/025801, International Search Report dated Sep. 30, 2015", 4 pgs.
(Continued)

*Primary Examiner* — Alicia Torres
*Assistant Examiner* — Adam J Behrens
(74) *Attorney, Agent, or Firm* — Schwegman, Lundberg & Woessner, P.A.

(57) ABSTRACT

A reaping based yield monitor system includes one or more reaping yield instruments configured for coupling with a harvester head. The one or more reaping yield instruments measure at least one crop characteristic of a harvested crop in sections of the harvester head. A yield monitor determines a variable yield of the harvested crop. An apportionment module apportions the variable yield of the harvested crop to the sections of the harvester head based on the at least one crop characteristic measured in each of the sections of the harvester head. In another example, a stand counting module counts a harvested standing crop with the one or more reaping yield instruments and a stand count output module output a harvested standing crop value based on one or more of the counted harvested standing crop or filtered measured values of a stand characteristic measured with the one or more reaping yield instruments.

36 Claims, 9 Drawing Sheets

Related U.S. Application Data

(60) Provisional application No. 61/979,839, filed on Apr. 15, 2014.

(56) References Cited

U.S. PATENT DOCUMENTS

| | | | |
|---|---|---|---|
| 5,801,948 A | 9/1998 | Wood et al. | |
| 5,864,781 A | 1/1999 | White | |
| 5,883,383 A | 3/1999 | Dragne | |
| 5,897,600 A | 4/1999 | Elmore et al. | |
| 5,884,205 A | 5/1999 | Elmore et al. | |
| 5,911,362 A | 6/1999 | Wood et al. | |
| 5,936,234 A | 8/1999 | Thomas et al. | |
| 5,938,071 A | 8/1999 | Sauder | |
| 5,969,340 A | 10/1999 | Dragne et al. | |
| 6,093,926 A | 7/2000 | Mertins et al. | |
| 6,185,990 B1* | 2/2001 | Missotten | A01B 79/005 |
| | | | 324/691 |
| 6,373,057 B1 | 4/2002 | Penfold | |
| 6,661,514 B1 | 12/2003 | Tevs et al. | |
| 6,951,514 B1* | 10/2005 | Coers | A01D 41/127 |
| | | | 460/1 |
| 6,983,217 B2* | 1/2006 | Moore | A01D 41/127 |
| | | | 701/50 |
| 7,089,117 B2* | 8/2006 | Maertens | A01D 41/127 |
| | | | 702/5 |
| 7,152,540 B1 | 12/2006 | Sauder et al. | |
| 7,472,660 B2 | 1/2009 | Mariman et al. | |
| 7,478,603 B2 | 1/2009 | Riewerts et al. | |
| 7,690,440 B2 | 4/2010 | Dean et al. | |
| 8,078,367 B2 | 12/2011 | Sauder et al. | |
| 8,141,504 B2 | 3/2012 | Dean et al. | |
| 8,170,825 B2 | 5/2012 | Beaujot et al. | |
| 9,144,195 B2* | 9/2015 | Koch | A01D 41/1272 |
| 9,213,905 B2* | 12/2015 | Lange | G06K 9/00805 |
| 2002/0133309 A1* | 9/2002 | Hardt | A01D 41/1271 |
| | | | 702/129 |
| 2003/0004630 A1 | 1/2003 | Beck | |
| 2011/0072773 A1 | 3/2011 | Schroeder et al. | |
| 2014/0230580 A1* | 8/2014 | Dybro | A01D 45/021 |
| | | | 73/865 |
| 2014/0331631 A1* | 11/2014 | Sauder | A01D 45/021 |
| | | | 56/10.2 R |
| 2015/0293068 A1 | 10/2015 | Acheson et al. | |

FOREIGN PATENT DOCUMENTS

| | | |
|---|---|---|
| EP | 0960558 A1 | 12/1999 |
| WO | WO-2013078328 A2 | 5/2013 |
| WO | WO-2015160837 A2 | 10/2015 |
| WO | WO-2015160837 A3 | 10/2015 |

OTHER PUBLICATIONS

"International Application Serial No. PCT/US2015/025801, Invitation to Pay Additional Fees and Partial Search Report dated Jun. 29, 2015", 2 pgs.

"International Application Serial No. PCT/US2015/025801, Written Opinion dated Sep. 30, 2015", 14 pgs.

"U.S. Appl. No. 14/687,723, Non-Final Office Action dated Jan. 24, 2018", 23 pgs.

* cited by examiner

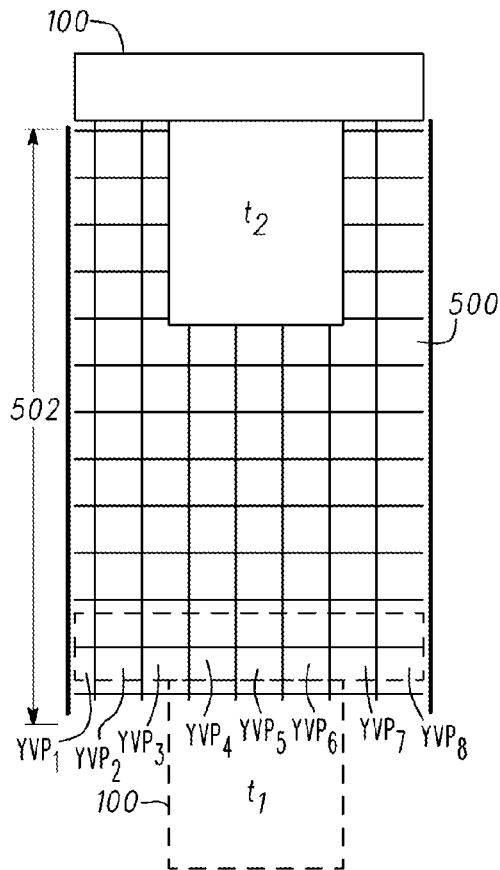
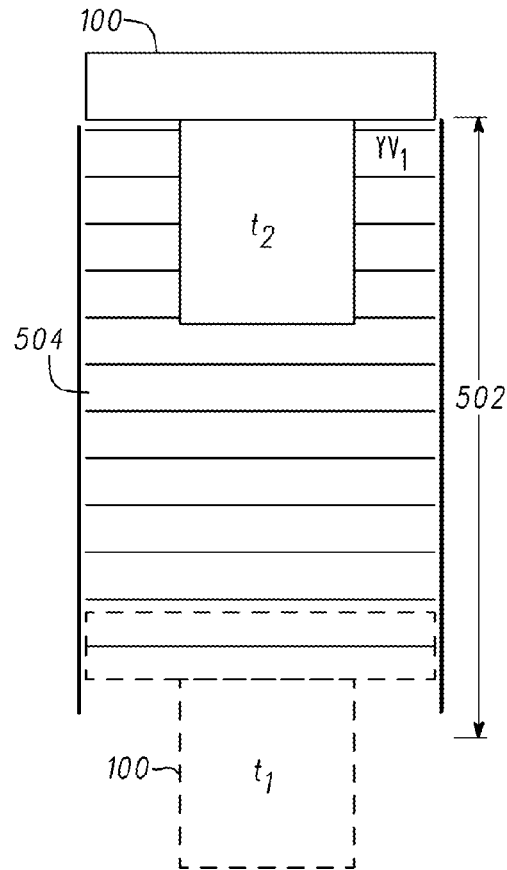
FIG. 5A
FIG. 5B
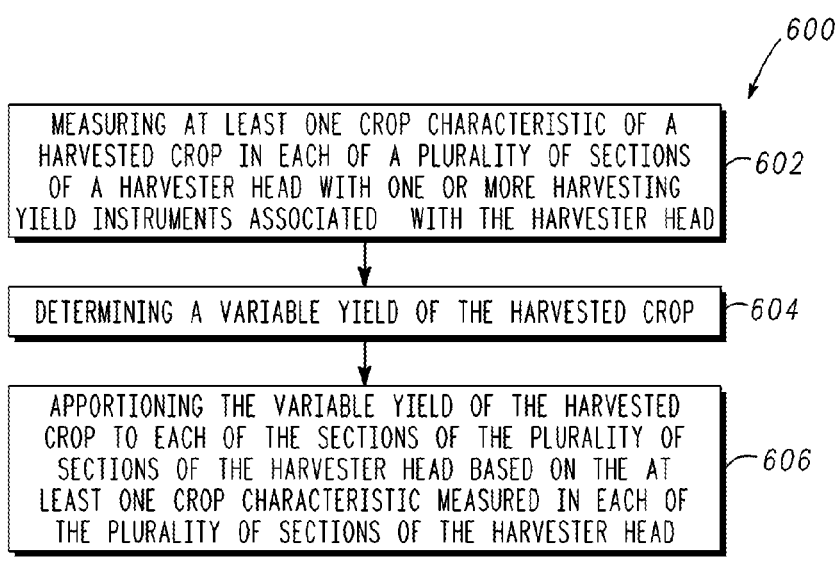
FIG. 6

REAPING BASED YIELD MONITORING SYSTEM AND METHOD FOR THE SAME

CROSS REFERENCE TO RELATED APPLICATIONS

This patent application claims the benefit of priority to U.S. Provisional Application Ser. No. 61/979,839, filed on Apr. 15, 2014, and claims the benefit of priority under 35 U.S.C. § 120 to Application Number PCT/US15/25801, filed Apr. 14, 2015, which applications are hereby incorporated by reference herein in their entirety.

COPYRIGHT NOTICE

A portion of the disclosure of this patent document contains material that is subject to copyright protection. The copyright owner has no objection to the facsimile reproduction by anyone of the patent document or the patent disclosure, as it appears in the Patent and Trademark Office patent files or records, but otherwise reserves all copyright rights whatsoever. The following notice applies to the software and data as described below and in the drawings that form a part of this document: Copyright Raven Industries, Sioux Falls, S. Dak. All Rights Reserved.

TECHNICAL FIELD

This document pertains generally, but not by way of limitation, sensors and systems associated with yield monitors

BACKGROUND

Agricultural harvesters (e.g., combines) provide a combination of functions used in harvesting a crop. In some examples, harvesters combine the functions of reaping, threshing and winnowing. Reaping is the cutting and gathering of crops, and threshing and winnowing is the loosening and subsequent separation of the edible part of the crop from the chaff.

Harvesters include interchangeable harvester heads. In some harvester heads a plurality of row sections are provided to facilitate the threshing of row based crops, including, but not limited to, corn, cotton, carrots, cabbage, sugar beets or the like. Individual rows of the crop are received within corresponding row sections and then gathered and cut. In a corn harvester head, for example, each corn stalk of a row is drawn into a channel of the row section by opposed chains and teeth, and at the same time the stalk is pulled downwardly through the channel by rotating spindles to separate the ears from the stalk. Downstream mechanisms within the harvester continue threshing and winnowing before delivery to a grain elevator.

Some harvesters include yield monitors provided near a grain elevator that lifts the threshed and winnowed crop to a bin at the rear of the harvester or in an adjacent trailer pulled by a tractor or truck. The harvested crop from each of a plurality of row sections of the harvester head is combined together and directed to the grain elevator. In some examples the yield monitors are associated with features of the grain elevator and measure the yield of the combined harvested crop as it is passed by the grain elevator.

OVERVIEW

The present inventors have recognized, among other things, that a problem to be solved can include decreasing inaccuracy of yield measurements in harvesters. For instance, yield monitors are in at least some examples associated with the harvester at the transition from threshing and winnowing to a bin (e.g., at or near a grain elevator on the harvester). Measuring a variable yield in an ongoing fashion at this location of the harvester may introduce error to the indexing of the yield to a corresponding portion of a field (e.g., a field or yield map). For instance, there is a time delay that varies between the time the crop is reaped (cut) and when it is received by a bin and measured with the yield monitor. During the time delay, the harvester continues to move and accordingly any indexed location for the variable yield on a field or yield map is offset according to the time delay and corresponding movement.

In an example, the present subject matter can provide a solution to this problem, such as by providing one or more harvesting (e.g., reaping) yield instruments and a matching module that accounts for time discrepancies between reaping from a field and yield measurements. The one or more reaping yield instruments are provided at the reaping or cutting station for the harvester, for instance at the harvester head. Accordingly measurements by the reaping yield instruments are taken at the location of the harvested crop and are not subject to a time delay or corresponding change in location. The one or more reaping yield instruments are included as part of a reaping based yield monitor system or yield measurement system. A matching module as part of the yield monitor (or a separate module communicating with the yield monitor) matches the measurements or time and location of the measurements of the one or more reaping yield instruments with a determined variable yield (an ongoing yield measured by the yield monitor). In one example, a specified time delay is used by the matching module to match the yield with one or more of the corresponding measurements, time or location of the reaping yield instruments. The specified time delay is determined and updated based on comparisons and matching of determined variable yield values with corresponding measurements of crop characteristics by the one or more reaping yield instruments. Based on the matching the determined variable yield is accurately associated with a location of the field (e.g., on a yield map) where the corresponding harvested crop was originally reaped.

In still another example, measurements of the one or more reaping yield instruments are taken over a window of time and updated during operation of the harvester. In one example, the measurements at a particular time (e.g., for a plurality of rows) are used to generate a characteristic value corresponding to a quantity or volume of the reaped crop, for instance by way of measuring impacts of ears of corn on impact sensors associated with row sections. The characteristic values are compared with corresponding variable yields of the harvested crop (e.g., measured with yield instruments at or near the harvester grain elevator). There is a proportional relationship between the characteristic values generated from measurements at the harvester head and the variable yields generated with the yield instruments near to the grain elevator. Based on this proportional relationship a corresponding particular characteristic value is matched with a (later in time generated) particular variable yield. The time and location of the characteristic value (based on the measurements of the one or more harvester yield instruments) facilitates indexing of the particular variable yield to the corresponding portion of the field where the crops were harvested. This information is indexed to a yield map to provide accurate yield mapping above and beyond previous yield monitor systems that failed to account for such a time discrepancy.

The present inventors have recognized, among other things, that another problem to be solved can include decreasing location based inaccuracy of yield measurements in harvesters (e.g., failure to map yield laterally). As discussed above, some examples of yield monitor systems measure yield based on a threshed and winnowed crop. The harvested crop is gathered from a plurality of sections of the harvester head and threshed and winnowed to loosen and remove chaff from the crop. The crop from each of the sections of the harvester head is then measured in a composite fashion by the yield monitor to determine a variable yield. The consolidation of the crop during threshing and winnowing prevents apportionment of yield between the plurality of sections (e.g., row sections) of the harvester head and prevents corresponding accurate indexing of the yield in a lateral manner across the field relative to the harvester head. Stated another way, yield monitors fail to provide lateral resolution for apportioned yield values across harvester heads.

In an example, the present subject matter can provide a solution to this problem, such as by providing the one or more reaping yield instruments (e.g., instruments associated with reaping tools or features) and an apportionment module that divides the determined variable yield across the plurality of sections of the harvester head according to the measurements of the reaping yield instruments. As discussed herein, the one or more reaping yield instruments are provided at the reaping or cutting station for the harvester, for instance at the harvester head. Accordingly, measurements by the reaping yield instruments are taken at the location of the harvested crop and are representative of measurements for each of the harvester head sections (e.g., row sections of a corn harvesting platform head). The one or more reaping yield instruments are included as part of a reaping based yield monitor system or yield measurement system. By matching the variable yield with the corresponding harvesting yield measurements taken at the harvester head (as described herein), the variable yield is apportioned (divided) between the plurality of sections based on the measurements of the one or more reaping yield instruments in each of the plurality of sections. Accordingly, variations in yield measured across a harvester head are determined and may be indexed to the field, for instance in a yield map. This variation is indexed to a yield map to provide accurate yield mapping in a lateral fashion according to the graduation of harvester head sections and instruments across the entire swath of the harvester head (e.g., based on a number or harvesting rows for the head, frequency of instruments on the head or the like). Indexing of yield values laterally across a harvester swath and with this degree of precision (e.g., according to sections) provides increased accuracy (resolution) to yield mapping relative to previous yield monitors.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIG. 5A is a schematic diagram of the harvester in a field harvesting a crop using the reaping based yield monitor system of FIGS. 1 and 2.

FIG. 5B is a schematic diagram of a harvester in a field harvesting a crop using another example of a yield monitor.

FIG. 6 is a block diagram of one example of a method for apportioning yield.

DETAILED DESCRIPTION

Figure 1:
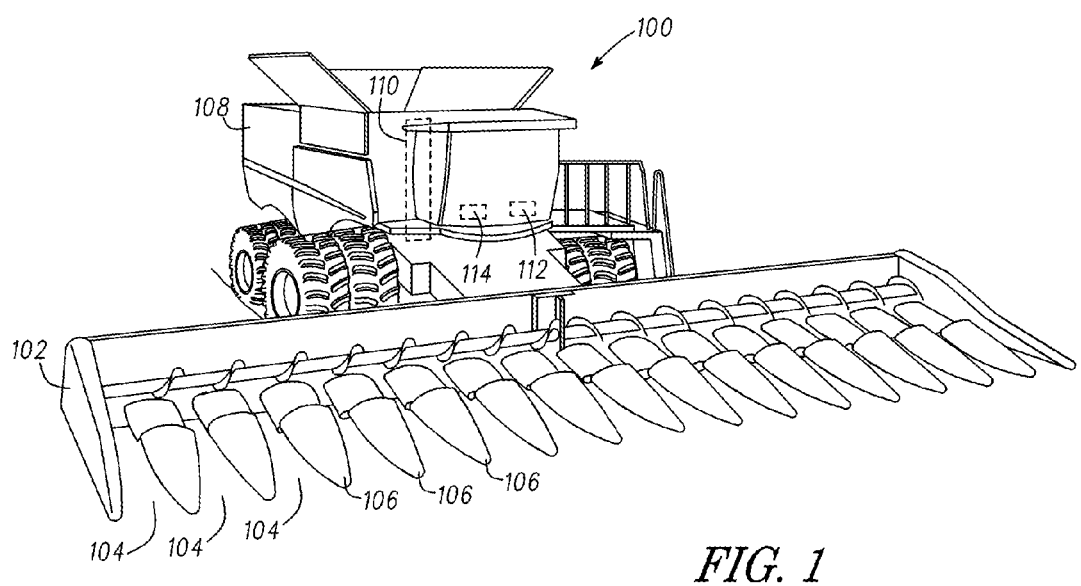
FIG. 1 is a perspective view of a harvester including one example of a reaping based yield monitor system.

The reaping based yield monitor system described by way of the examples herein determines the relative grain yield per section in a multi-section (e.g., multi-row) harvester. In one example, the system utilizes sensors coupled with a harvesting head (e.g., a corn harvesting head) that detect the relative quantity of grain harvested by each section of a harvester head (e.g., each section or row section of a harvester head). The relative quantity of a harvested crop entering each row of the harvester is measured and used to improve yield placement accuracy of an existing grain yield monitor or mapping system. The systems described herein are useful for row based crops including, but not limited to, corn, cotton, carrots, cabbage, sugar beets or the like. Additionally, the systems described herein are used with other harvester arrangements including elongate harvester heads configured for non-row based harvesting, such as soy beans, wheat or the like, where the harvester head is divided into sections or zones for instance by laterally scans available with some instruments (e.g., imaging, optical, infrared and ultrasonic or the like). For instance a harvester head has a width, and each of the instruments is configured to measure a crop characteristic within a portion (section) of that width.

There are multiple instruments that are utilized as one or more reaping yield instruments (e.g., yield instruments configured to measure a crop characteristic at or near to the time of reaping) to measure a yield characteristic for each section (e.g., each row section). Examples of reaping yield instruments include, but are not limited to, force plates, impact sensors, infrared (IR) sensors, optical non-contact sensors, non-contact infrared sensors, video sensor networks, a single camera having a distributed viewing arc, or the like.

Load cells or force impact sensors as the one or more reaping yield instruments are installed near each of a plurality of sections of the harvester head. For instance, impact sensors or load cells are coupled with the deck plates of each of the row sections of a corn harvester head. One or more of the relative force of impacts or the number of impacts are detected from ears of corn as they contact the deck plates (and the sensors provided therein) to determine one or more harvested crop characteristics that corresponding to the relative yield for a section of the harvester head (e.g., a row section of the harvester head).

In an example, the one or more reaping yield instruments include infrared or optical sensors. The sensors are coupled in a plurality of sections of the harvester head (e.g., in each row section of a corn harvester head). The sensors measure one or more characteristics corresponding to a volume of harvested crop entering each section or row section. These measured characteristics are used to determine or approximate the relative quantity of a crop harvested by each section (e.g., a row section corresponding to a row in a field).

In another example, the one or more reaping yield instruments include a video sensor network having, for instance, a camera mounted on or adjacent to the sections of a harvester head, such as the row sections of a corn harvester head. The cameras pass the ongoing images or video footage of harvesting of the crop to a processing module (e.g., as a measured crop characteristic) for estimation of the relative flow of the crop for each section (e.g., row section). In one example, the processing module is part of a yield monitor or reaping instrument controller of the reaping based yield monitor system. The characteristics are used to determine the relative quantity of a crop harvested by each section (e.g., a row section corresponding to a row in a field). In still another example, the one or more reaping yield instruments include a single stream video camera having a single or (fewer cameras than sections of the head) mounted on the harvester with a view of each section of the plurality of sections (in a corn harvester head, each row section). The single stream video camera passes a video stream of each of the plurality of sections into a processing module (e.g., as a measured crop characteristic). The processing module (e.g., as part of a yield monitor or a reaping instrument controller) determines or approximates the relative yield of each row from the information captured in the video stream.

Accordingly, the one or more reaping yield instruments (e.g., configured to measure crop characteristics on a section by section or lateral basis) is able to provide increased resolution of yields, for instance according to the yield of each row of a field. In one example, the generated yield values for each of the sections is plotted to a yield map to increase the resolution of a yield map beyond indexing of an overall total yield of a grain elevator.

As described herein, in one example, the one or more reaping yield instruments and a reaping instrument controller communicate with a yield monitor (e.g., associated with a harvester grain elevator). The yield monitor generates yield values by way of instrumentation near to the grain elevator and associates the yield value with corresponding crop characteristics from the reaping yield instruments at the harvester head. The overall yield is apportioned between the sections of the plurality of sections based on the measured crop characteristics observed by the reaping yield instruments. In one example, the reaping instrument controller includes modules configured to interpret the crop characteristics of the one or more harvesting instrument and transmit the values to the yield monitor and also apportion the yield values generated by the yield monitor. In another example, the yield monitor includes the modules for interpreting the measurements of the reaping yield instruments and apportioning the yield values between the sections (e.g., row sections).

In addition to improved row resolution for yield results, the reaping based yield monitor systems described herein improve the allocation of yield totals to accurate position of the harvester. That is to say, by measuring crop characteristics as the crop is reaped the yield values are accurately mapped to the location on the field where the corresponding crops were harvested. Time delays for threshing and winnowing and subsequent measurement of yield values are effectively eliminated and indexing of the yield values occurs accurately to the corresponding portions of the field (e.g., generally to a previous location of the harvester based on the time for threshing, winnowing and yield value measurement).

For instance, some examples of yield monitoring systems include a varying yield delay to accommodate the processing time between when the crop is reaped to when it is threshed, winnowed and then measured by the yield instruments (e.g., near to or within the harvester grain elevator). This delay time typically ranges between 10 and 20 seconds and is dependent on many factors in the construction of the harvester and its configuration (e.g., type of harvester head). Any error in this yield delay time estimate leads to yield placement (indexing) inaccuracies along the direction of travel of the harvester. The reaping based yield monitor systems described herein address these inaccuracies by facilitating the matching of determined variable yield values from the yield monitor to prior measurements of the one or more reaping yield instruments. For instance, trends and relationships are detected between the ongoing yield values generated by the yield monitor and the ongoing measurements of the one or more reaping yield instruments. By noting correspondence between both (e.g., yield to measured crop characteristics, such as volume or flow rate, frequency of impacts with a contact instrument or the like) the determined variable yield is accurately indexed to the corresponding measured crop characteristics at the time the crop characteristics were measured. Accordingly, the yield is then indexed to that corresponding portion of the field that was cut at the time the measurements were taken by the reaping yield instruments. Optionally, indexing allows for the determination of a time delay in an ongoing accurate fashion. The time delay is then used to associate the determined variable yield with measured crop characteristics from the reaping yield instruments at the appropriate time.

Optionally, the subject matter described herein is applicable with, but not limited to, Raven SmartYield Enhancement. The subject matter described herein provides enhanced yield resolution in the forward and lateral directions, an ear count feature for ear count mapping (ears per stalk or area) and an ear sizing feature for ear size estimation (estimation of size of each ear). Further, the subject matter described herein is provided in another example as an aftermarket product configured for incorporation with third party existing yield monitors. For instance, the reaping based yield monitor system includes one or more reaping yield instruments and a reaping instrument controller that acts as a yield monitor interface. The interface includes the modules used for interpretation of measurements taken by the reaping yield instruments and also includes matching and apportionment modules used to match the determined variable yield (from the yield monitor) with corresponding measurements of the one or more reaping yield instruments and accordingly divide the yield across the sections laterally. In another example, the matching and apportionment modules (as a reaping instrument controller) are incorporated into the yield monitor (e.g., by jump drive, uploading or the like) to configure the yield monitor for use with the reaping yield instruments. The coupling between the yield monitor, the one or more reaping yield instruments and the reaping instrument controller includes one or more of wired or wireless connection (e.g., cabling, buses, CAN bus, Ethernet, Bluetooth, RF or the like). Accordingly, existing yield monitors are updated and enhanced to facilitate the generation of high resolution yield maps that provide precise and accurate yield values at accurate locations (e.g., down to individual crop rows or sections of a field). The high resolution yield maps are used to generate subsequent high resolution planting and agricultural product application schemes (e.g., field maps) for use by planters, spreaders or the like.

Optionally, the system described herein including the one or more reaping yield instruments and a reaping instrument controller (e.g., a harvester header processor or dedicated yield monitor) is provided as a standalone system to provide real time accurate estimates of crop characteristics, such as ear counts, unthreshed and unwinnowed crop flow rates, or the like that are accurately apportioned between the plurality of sections of the harvester according to the measurements provided by the reaping yield instruments.

Some benefits of these systems (e.g., a yield monitor system or measuring system for coupling with a yield monitor) include, but are not limited to:

Higher accuracy yield placement by a yield monitor in a side to side (lateral) basis and forward and reverse travel (e.g., because of accurate indexing of yield values based on measurements of the reaping yield instruments).

Corn ear count numbers are estimated allowing for additional information to be provided by the yield monitor. In one example, the one or more reaping yield instruments include one or more impact or contact sensors associated with deck plates of the row sections of a harvester. Each contact or impact is measured as an ear of corn. As discussed herein, such a system is optionally used in a standalone fashion (without or independently from a yield monitor of the harvester) to measure crop yield results in the format of quantity of ears of corn.

Allows for installation to existing and third party yield monitors as an enhancement for more accurate yield monitoring and indexing to yield maps (e.g., lateral accuracy across a swath of the harvester, and temporal accuracy based on association of the yield with corresponding crop characteristics measured at the harvester head as the crop is harvested).

FIG. 1 shows one example of harvester 100, such as a combine, used in an agricultural field to harvest one or more crops and further process the crops by threshing and winnowing the crops for eventual deposition within a grain bin 108. Referring again to FIG. 1, the harvester 100 includes a harvester head 102 including a plurality of tools thereon, for instance one or more row sections 104 configured to reap and thresh crops harvested from a field. In the example shown in FIG. 1, the row sections 104 are set up on the harvester head 102 in the manner of a corn harvesting head. Each of the row sections 104 are bracketed by snouts 106 provided to either side of the tools used in the row sections 104 for removal of the stalk from the ears of the corn. The harvester head 102 further includes one or more augers that carry the ears of corn centrally toward the harvester 100. As further shown in FIG. 1, in one example the harvester 100 includes a grain elevator 110. The grain elevator 110 lifts the harvested crop (ears of corn, wheat, soybeans, cotton or the like) from a lower position in the harvester 100 to an upper position such as a spout that empties the harvested crop into the grain bin 108.

Referring again to FIG. 1 the harvester 100 is shown in this example with a yield monitor 112. In one example, and as described herein the yield monitor 112 communicates with one or more yield instruments for instance yield instruments that are associated with the grain elevator 110. The yield monitor 112 with the associated yield instruments is configured to measure the yield of the harvested crop at the grain elevator 110 prior to delivery of the harvested crop to the grain bin 108. In one example, the harvested crop is measured as the crop enters the grain elevator 110 and ascends to a spout for delivery to the grain bin 108. As further shown in FIG. 1, the grain elevator 110 (and the associated yield instruments) are downstream relative to the harvester head 102. As further described herein, in one example the harvester head 102 or components of the harvester 100 adjacent to the harvester head 102 include one or more reaping yield instruments configured to measure one or more crop characteristics of the harvested crop (e.g., volume of crop, quantity of impacts by ears of corn or the like) as it is reaped by the harvester head 102. The reaping based yield monitor system described herein works with the determined yield value, for instance generated by the yield monitor 112 to apportion the yield value to each of the row sections 104 according to measurements taken by each of the reaping yield instruments at each of the row sections 104 (or at one or more sections along the harvester head 102 in the case of a harvester head like a grain harvester head). In one example, the apportionment of the variable yield thereby enhances the resolution of yield values across the harvester head 102 for instance with a resolution equal to the number sections or row sections 104. That is to say, the yield value determined by the yield monitor 112 is apportioned based on the the measured values of the one or more crop characteristics taken at each of the row sections 104 (or sections where row sections are not included with the harvester head 102) to thereby apportion the variable yield into variable yield portions totaling to a value equal to the yield generated by harvesting at across all of the row sections 104.

In one example, the reaping yield monitor system includes a reaping instrument controller for instance a module or separate standalone component in communication with each of the reaping yield instruments provided along the harvester head 102. The reaping instrument controller is in one example included with the yield monitor 112 or as a software package or separate add-on module coupled with the yield monitor 112. In another example, the reaping instrument controller is a separate module in communication with the yield monitor 112 for instance with a system bus or controller area network (CAN) bus. By facilitating communication between the yield monitor 112 and the reaping instrument controller (in communication with the reaping yield instruments) the determined variable yield generated by the yield monitor 112 is apportioned across the harvester head 102 as described herein.

Further, in another example the reaping yield instruments at the harvester head 102 are upstream relative to the yield instruments provided at the grain elevator 110. Accordingly, the measurements of the crop characteristic taken by the reaping yield instruments at the row sections 104 are taken at a contemporaneous time the harvesting of the crop from the field. In another example, the reaping based yield monitor system is able to backdate the variable yield generated by the yield monitor 112 to the time of the actual harvesting of the crop for instance at the harvester head 102. By backdating the variable yield to the time of harvesting of the corresponding crops that are the basis of the variable yield at the variable yield monitor 112 indexing of the apportioned variable yield is possible not only across the row sections 104 but also in an accurate manner to the corresponding portion of the field (e.g., on a field map). In contrast, previous yield monitors 112 indexed yield values to the field map at a later portion of the field for instance according to the lag time between harvesting at the harvester head 102 and measuring of the yield value for instance with the yield instruments associated with the grain elevator 110 (and after processing such as threshing and winnowing).

Figure 2A:
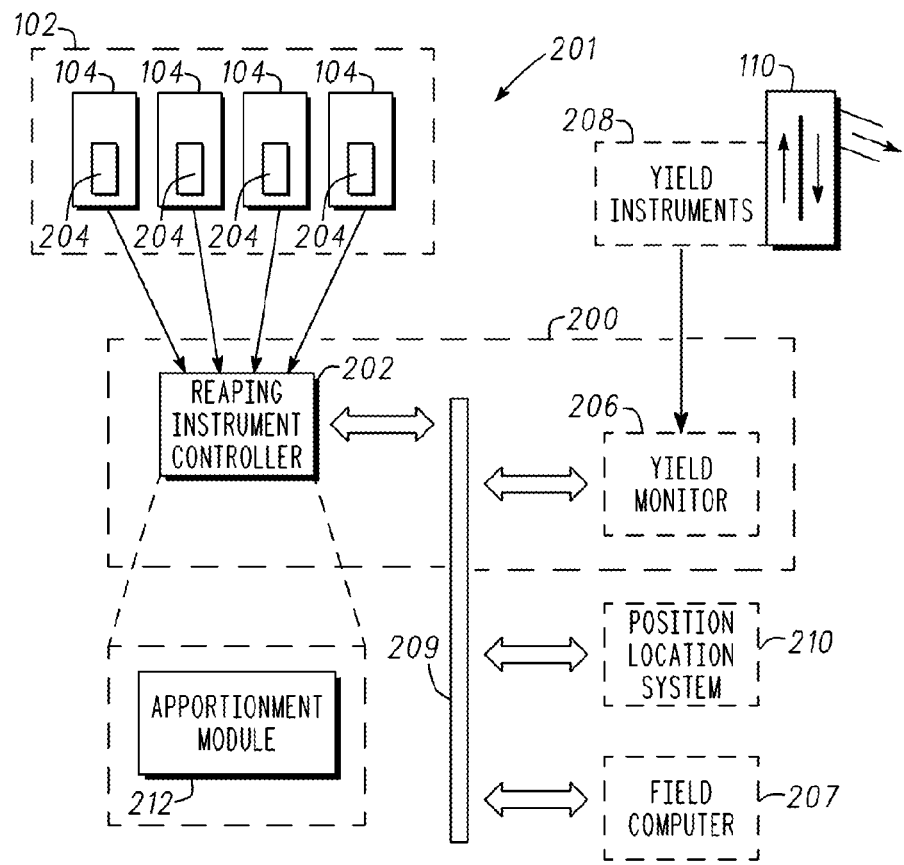
FIG. 2A is a schematic view of one example of the reaping based yield monitor system of FIG. 1.

One schematic example of a control system 201 for the harvester including a reaping based yield monitor system 200 is shown in FIG. 2A. As shown, the reaping based yield monitor assembly 200 includes a reaping instrument controller 202 associated with a plurality of reaping yield instruments 204 (e.g., one or more reaping yield instruments) associated with sections of the harvester head 102, such as each of the row sections 104. In the example shown in FIG. 2A, an exemplary four row sections 104 are provided. In another example, for instance with a harvester head having 18 or more row sections a corresponding number of reaping yield instruments 204 for instance 18 yield instruments are provided for each of the row sections 104.

In another example, the reaping yield instruments 204 (e.g., one or more reaping yield instruments) are provided across a plurality of sections. For instance the reaping yield instruments 204 include one or more imaging or optical sensors configured to observe a plurality of sections of the harvester head and thereby generate corresponding data for each of the sections.

As will be described herein, in yet another example the reaping yield instruments 204 include mechanical contact sensors (e.g., load cells, strain gauges or the like) configured to register and measure impacts of the crop against one or more sensor features for instance impact plates. In one example, the reaping yield instruments 204 include impact plates sized and shaped to receive impacts from corn ears striking the impact plates as the stalk is drawn through the row section 104 during harvesting. The impact plates include sensors, such as load cells, strain gauges or the like, configured to identify one or more characteristics including, but not limited to, the number of impacts, force of the impacts or the like.

As further shown in FIG. 2A, the reaping based yield monitor assembly 200 optionally includes a yield monitor 206 (shown in dashed lines to indicate the optional inclusion of the yield monitor 206) interfaced with the reaping instrument controller 202 for instance with an interface 208 such as a bus, CAN bus or the like. As previously described herein, the yield monitor 206 in one example is coupled with a plurality of yield instruments 208 associated with the grain elevator 110. As previously described the yield instruments 208 are downstream from the row sections 104 and the reaping yield instruments 204 provided at each of the row sections 104. Accordingly yield values generated by the yield instruments 208 are delayed (by threshing, winnowing, transport and measurement of the yield values) relative to corresponding measurements taken by the reaping yield instruments 204 at the harvester head 104.

Optionally, the reaping instrument controller 202 is incorporated with the yield monitor 206. In another example the reaping instrument controller 202 is a separate module coupled with each of the reaping yield instruments 204 and separately coupled to the yield monitor 206 for instance by way of the interface 208. In still another example the reaping instrument controller 202 is a software module or software package incorporated with the yield monitor 206 (e.g., provided by CDROM, jump drive, a network connection, wireless downloading or the like).

Referring again to FIG. 2A, in one example the control system 201 includes a position location system 210 (GPS or RTK transmitter and receiver or the like) in communication with one or more of the components of the control system 201 for instance with the interface 208. In another example, the control system 201 includes a field computer 207 for instance including one or more of field maps, planting maps, automated steering algorithms or other control algorithms for use with the harvester. The field computer 207 in one example is configured to communicate with one or more of the reaping based yield monitor assembly 200 (including the reaping instrument controller 202 and yield monitor 206) as well as the position location system 210 by way of the interface 208. Optionally the position location system 210 is incorporated with the field computer for instance as a component of the field computer configured to operate with the field computer for instance for automated steering (steering or navigation cues for the operator) and automated control of the harvester.

FIG. 2A includes a detailed view of one example of the reaping instrument controller 202. In the detailed view the reaping instrument controller 202 includes at least one module, in this example an apportionment module 212. As will be described herein the apportionment module 212 of the reaping instrument controller 202 associates measurements of the reaping yield instruments 204 for instance measurements of one or more crop characteristics (e.g., volume flow rates through the sections, ear impacts, force of impacts or the like) to yield values generated by the yield monitor 206 in combination with the yield instruments 208. As previously described herein the yield values generated by the yield monitor 206 are generated at a second later time relative to the corresponding measurements taken by the reaping yield instruments 204 at the row sections 104. The apportionment module 212 further divides the generated yield (e.g., an ongoing variable yield) across each of the row sections 104 according to the measurements of the crop characteristic at each of the reaping yield instruments 204. That is to say, the apportionment module 212 divides the determined variable yield generated by the yield monitor 206 into variable yield portions that vary for each of the row sections 104 according to corresponding crop characteristic measurements taken by the reaping yield instruments 204 at an earlier time (e.g., reaping of the crop that serves as the basis for the later yield value).

In another example the apportionment module 212 of the reaping instrument controller 202 is configured to index the variable yield (e.g., the variable yield portions divided across the row sections 104) according to the association of the generated yield value at the yield monitor 206 to the corresponding measurements of the crop characteristic at the reaping yield instruments 204. For instance, as previously described herein the reaping yield instruments 204 conduct their measurements at a first time corresponding to the reaping of the crop from the field while the yield monitor 206 generates the corresponding yield value at a second later time (according to threshing, winnowing, transport of the crop and the like). The association of the measurements of the reaping yield instruments 204 with the corresponding yield value at the yield monitor 206 automatically indexes the yield value to the previous first time corresponding to the measurement of the crop characteristics by the reaping yield instruments 204 (and reaping). In another example, the association of the measurements of the reaping yield instruments 204 to the variable yield determined with the yield monitor 206 is used to determine a delay time, and the delay time is used with ongoing variable yield measurements generated by the yield monitor 206 to accurately apportion the yield across the section and index the variable yield portions to the corresponding parts of the field (e.g., a field map).

By associating the determined variable yield with the one or more measurements taken by the reaping yield instrument 204 and processed by the reaping instrument controller 202 the variable yield is accurately paired to the time of harvesting of the corresponding crops that generated the variable yield value. By pairing the later determined variable yield with the measured crop characteristics of the reaping yield instruments 204 at the earlier time of the crop harvesting the variable yield (e.g., variable yield portions apportioned across the row sections 104), is accurately indexed to a field map contemporaneously to the time of the actual crop harvesting. Field maps including this enhanced indexing thereby provide a more accurate representation of the harvest with yield values accurately located throughout the map. That is to say, the reaping based yield monitor assembly 200 described herein is able to not only apportion the variable yield across a plurality of sections such as the row sections 104 and thereby provide increased lateral resolution for yield values, the assembly 200 is also able to accurately index the variable yield determined by the yield monitor 206 to the appropriate time and location of a field from which the harvested crop that generated the yield value was reaped.

The reaping instrument controller 202 optionally includes additional modules or elements configured to interface with one or more of the one or more reaping yield instruments 204, the interface 208 and corresponding other features coupled with the interface 208 such as the yield monitor 206. For instance, in one example the reaping instrument controller 202 includes a processing module in communication with each of the one or more reaping yield instruments 204. The processing module receives and interprets raw measurement data corresponding to values of one or more crop characteristics (volume flowrates, impact counts, impact forces or the like) measured by the reaping yield instruments 204 and processes the values into data for use by the controller 202, for instance with the apportionment module 212. In another example, the reaping instrument controller 202 includes a time stamping module configured to apply a time stamp to each of the one or more measurements conducted by the reaping yield instrument 204 according to the time the measurement is generated at each of the instruments 204. In one example, the time stamp provided to the measurements of the reaping yield instruments 204 is used to consolidate the measurements from the instruments into a corresponding characteristic value (having a corresponding time) for comparison with the yield value generated at the yield monitor 206. In another example, the time stamp for the measurements is used with regard to a supplemental time stamp associated with the variable yield generated at the yield monitor 206. The time stamps for corresponding to a first time for the measurements of the reaping yield instruments 204 and a second time of generation of the variable yield for instance at the yield monitor 206 are used to accordingly backdate the variable yield (e.g., for instance variable yield portions apportioned across the row sections 104) to the corresponding time of the measurements of the reaping yield instruments 204. When used in combination with the speed and location information of the harvester 100 (e.g., with the position location system), the backdated variable yield value is accurately indexed to the appropriate portion of the field (e.g., a corresponding location on a field map).

Figure 2B:
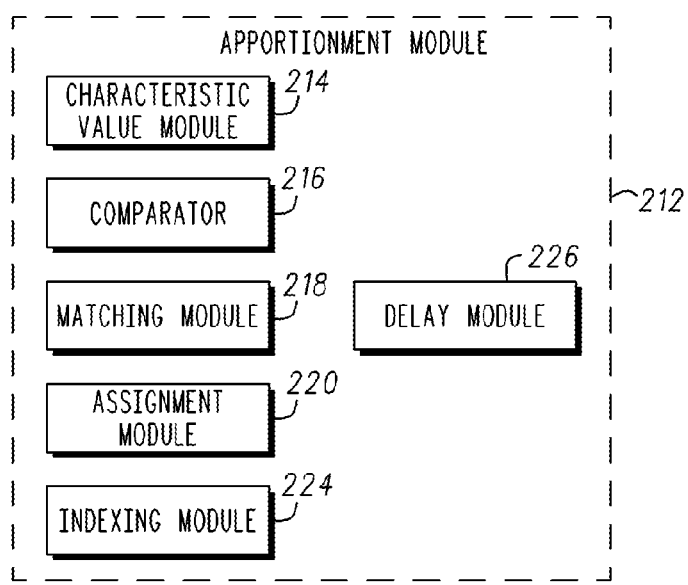
FIG. 2B is a detailed schematic view of a portion of a reaping based yield monitor assembly.

FIG. 2B shows one example of the apportionment module 212 previously shown and described in FIG. 2A. As shown the apportionment module 212 includes a plurality of sub-elements or modules configured to apportion the variable yield such as the variable yield generated at the yield monitor 206 to one or more sections corresponding to the sections of the harvester head 102. In another example, the apportionment module 212 includes an indexing module 224 configured to index the apportioned variable yield (e.g., variable yield portions assigned to sections) to corresponding sections of a field map for a field. For instance, in one example the indexing module 224 indexes the variable yield portions to corresponding portions of a field map to provide a graphical or tabular representation of the apportioned variable yield for a plurality of locations of a field, such as a continuous plurality of locations to thereby map the entirety of the variable yield portions throughout the field. The resulting field map including these variable yield portions provides a high resolution field map and accordingly provides an enhanced representation of the variable yield as it is apportioned across the field for instance with resolution at least as fine as a section of the harvester head 102, for instance a row section 104 corresponding to one crop row (e.g., a crop row of corn).

Referring again to FIG. 2B, the apportionment module 212 of the reaping instrument controller 202 included with the reaping based yield monitor assembly 200 includes a characteristic value module 214. In one example the characteristic value module 214 receives a plurality of values corresponding to measurements taken by the reaping yield instruments 204 at a first time. The characteristic value module 214 consolidates the plurality of values (e.g., $V$), $V_2$, $V_3$, $V_4$, $V_n$ and the like) into an ongoing consolidated value ($CV_1$) corresponding to the measurements of the crop characteristics taken with each of the reaping yield instruments 204. In one example, the ongoing consolidated values ($CV_n$) are generated in an ongoing fashion for instance, automatically and a plurality of times as the harvester 100 moves through a field and accordingly continues to harvest crop from the field. The ongoing consolidated values thereby provide an ongoing (optionally continuous) representation of the measurements of the reaping yield instruments 204 in a consolidated fashion. The plurality of values ($V_n$) and the corresponding ongoing consolidated values ($CV_n$) are time stamped for use in comparison with one or more yield values generated with the yield monitor 206 and the yield instruments 208 (see FIG. 2A).

The apportionment module 212 includes in another example a comparator 216. The comparator 216 compares the determined variable yield values for instance a yield generated by the yield monitor 206 ($YV_n$) at a second time with the plurality of ongoing consolidated values ($CV_n$) generated with the characteristic value module 214. As previously described herein the variable yield generated with the yield monitor 206 with the yield instruments 208 is taken at a second later time relative to the harvesting of the corresponding crops at the row sections 104. That is to say, the yield monitor 206 and yield instruments 208 associated in one example with a grain elevator 110 are positioned at a downstream location relative to the reaping yield instruments 204. Accordingly, the variable yield generated by the yield monitor 206 is generated at a second later time relative to the first time the measurements are taken at the reaping yield instruments 204 (e.g., at the time of reaping). In one example, each of the variable yield values ($YV_n$) generated in an ongoing fashion by the yield monitor 206 is compared with a plurality of ongoing consolidated values ($CV_n$) generated by the characteristic value module 214. In one example, one or more of curve fitting, comparative algorithms or the like are used to compare the ongoing consolidated values ($CV_n$) with the variable yield values ($YV_n$) generated by the yield monitor 206. Based on this comparison an instant variable yield value (e.g., a determined variable yield) generated by the yield monitor 206 is matched to the closest corresponding ongoing consolidated value generated by the characteristic value module 214, for instance with the matching module 218.

In one example, the yield monitor 206 generates a continuous or near continuous series of ongoing yield values (e.g., $YV_1$, $YV_2$, $YV_3$, $YV_4$, $YV_n$ and on the like). As previously described herein these yield values $YV_n$ are taken at later times relative to corresponding ongoing consolidated values $CV_n$. The comparator 216 compares each of the yield values $YV_n$ with each of the ongoing consolidated values $CV_n$ to accordingly associate or match a determined variable yield value $YV_n$ with the closest corresponding ongoing consolidated value $CV_n$. As discussed herein, the operation of the characteristic value module 214, the comparator 216 and the matching module 218 is conducted on a continuous basis to associate the yield values ($YV_n$) generated at the yield monitor 206 with the corresponding measurements taken at the reaping yield instruments 204 by way of the consolidated values $CV_n$. In another example the matching of the determined variable yield values with the corresponding ongoing consolidated values is conducted at an infrequent basis and a delay time is measured, for instance with delay module 226 in communication with the matching module. The delay time measured by the delay module 226 is used to automatically backdate the variable yield values generated with the yield monitor 206 and the yield instruments 208 (see FIG. 2A) to an estimated time of harvesting for instance harvesting conducted by the harvester head 102. In such an example the variable yield value is then apportioned to each of the sections such as the row sections 104 according to the corresponding measurements of the reaping yield instruments 204 taken at the backdated time (determined according to the delay time).

As further shown in FIG. 2B the apportionment module 212 in one example includes an assignment module 220. The assignment module 220 divides the now matched determined variable yield value ($YV_n$ taken at a second later time) based on the corresponding measurements of the reaping yield instruments 204 ($V_1$, $V_2$, $V_3$, $V_4$, $V_n$ taken at a first time). The determined variable yield value is divided into each of sections (e.g., row sections) according to the corresponding measurements. That is to say, the assignment module 220 divides the matched determined variable yield value into variable yield portions ($VYP_1$, $VYP_2$, $VYP_3$, $VYP_4$, $VYP_n$ summing to $YV_n$) between each section of the plurality of sections of the harvester head 102 according to the one or more measurements taken by the reaping yield instruments 204 across the harvester head 102 $V_1$, $V_2$, $V_3$, $V_4$, $V_n$). Stated another way, the variable yield value $VYP_1$, $VYP_2$, $VYP_3$, $VYP_4$, $VYP_n$ generated with the yield monitor 206 is a yield value corresponding to a consolidated yield for the crops harvested by each of the sections of the harvester head 102 (e.g., the row sections 104 with a corn harvester head 102). The yield value ($YV_n$) generated by the yield monitor 206 is apportioned in an accurate and precise manner between each of the row sections 104 (to $VYP_1$, $VYP_2$, $VYP_3$, $VYP_4$, $VYP_n$) based on the measurements in each section ($V_1$, $V_2$, $V_3$, $V_4$, $V_n$) to accordingly provide varied component yield values across the harvester head 102 (that sum to the associated and matched yield value $YV_n$). The accurately assigned variable yield portions provided enhanced resolution to a corresponding field map according to the size of the sections. In the case of a corn harvester head 102 with row sections 104 and reaping yield instruments 204 associated with each of the row sections 104 the reaping based yield monitor assembly 200 has a lateral resolution across a harvester head of a row section 104 corresponding to a crop row on the field. Accordingly, harvester heads that have 18 or more row sections 104 are able to provide lateral resolution of yield corresponding to a section of the head 102, for instance a single row section 104.

In another example, the reaping instrument controller 202 includes an indexing module 224. The indexing module 224 is in communication with a field computer such as the field computer 207 including a field map therein. In another example, the indexing module 224 has access to a field map for instance a field map associated with or stored by the reaping instrument controller 202. The indexing module 224 is configured to map the variable yield portion values ($VYP_1$, $VYP_2$, $VYP_3$, $VYP_4$, $VYP_n$) assigned to each of the plurality of sections of the harvester head 102 to corresponding portions of a field map corresponding to the location of each of the harvester head 102 sections at the time of harvesting of the crop (e.g., a first time), the same time as measurement of the one or more crop characteristics with the reaping yield instruments 204.

In one example, where the delay time is determined with the delay module 226 the delay time is used by the indexing module 224 in combination with the known speed of the harvester 100 to associate the variable yield portions ($VYP_1$, $VYP_2$, $VYP_3$, $VYP_4$, $VYP_n$) assigned to each of the corresponding sections of the harvester head 102 (e.g., row sections) to corresponding locations on the field (crop rows) associated with the location of the harvester 100 at the first time (the time the reaping yield instruments 204 conducted the measurements of the at least one crop characteristic). Stated another way, with a combination of the delay time and the speed of the harvester 100 the variable yield portions of the determined variable yield value ($YV_n$) are accurately assigned to areas of the field map corresponding to the position of the harvester when the associated crops (resulting in the yield value $YV_n$) were harvested. In another example, the indexing module 224 is in communication with the position location system 210 (e.g., a GPS system, real time kinematic (RTK) system or the like) and has access to a series of logged locations of the harvester 100 at a plurality of times including a first time corresponding to the first time the values of the at least one crop characteristic ($V_1$, $V_2$, $V_3$, $V_4$, $V_n$ taken at a first time) are measured by the reaping yield instruments 204. After association of the variable yield with the corresponding ongoing consolidated value (e.g., as described with the comparator 216 and the matching module 218) the ongoing consolidated value associated with the variable yield is known and accordingly the first time is also known. By matching the first time of the ongoing consolidated value with the corresponding location of the harvester 100 at the first time the apportioned variable yield (VYP$_1$, VYP$_2$, VYP$_3$, VYP$_4$, VYP$_n$) apportioned across the row sections 104 and the harvester head 102 is indexed to the previous location of the harvester 100 at the first time.

As described herein and shown for instance in FIGS. 2A and 2B, the reaping based yield monitor system 200 including the reaping instrument controller 202 and the one or more reaping yield instruments 204 associated with the harvester head 102 accurately and with increased resolution plots an apportioned variable yield (VYP$_1$, VYP$_2$, VYP$_3$, VYP$_4$, VYP$_n$) across the harvester head 102 (for instance in a manner corresponding to crop rows on a field map) and does with the variable yield portions indexed to corresponding portions of the field from which the harvested crop that generated the variable yield value was harvested. That is to say the reaping based yield monitor assembly 200 is not only able to provide increased resolution of the variable yield value, for instance across a plurality of sections of a harvester head 102, the reaping based yield monitor system 200 also accurately associates the variable yield value to the corresponding portion of the field from which the crop was harvested (e.g. through the use of a delay time, association of the yield value to the consolidated value $CV_n$ or the like in combination with the known speed of the harvester 100, logged locations with the position location system 210 or the like). Accordingly the reaping based yield monitor system 200 described herein is able to provide enhanced resolution and accuracy for the mapping of the variable yield of the harvested crop to a field map.

Figure 3A:
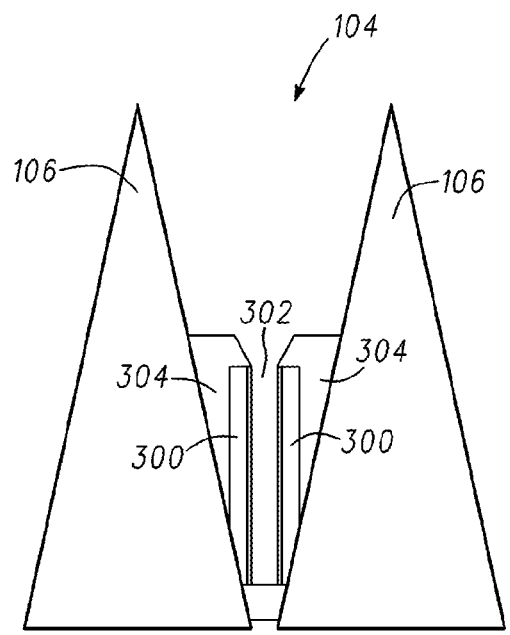
FIG. 3A is a schematic top view of one example of a row section of a harvester head.

FIG. 3A shows one schematic view of a row section 104 of the harvester head 102 shown in FIG. 1. As shown, the row section 104 includes snouts 106 on either side of a section gap 302. The section gap 302 allows for the reception of corn stalks therein for reaping (e.g., to remove ears of corn and cutting of the stalk). As previously described herein, each of the row sections 104 of the harvester head 102, in one example, includes a reaping yield instrument 204. In the example shown in FIGS. 3A-D, the reaping yield instrument includes a contact instrument 300 provided with at least one of the strike plates 304 to sides of the section gap 302. As will be described herein, in one example the contact instruments 300 measure one or more crop characteristics of the crop as the crop is reaped from the field. For instance as the stalk of the cornstalk is drawn through the section gap 302 (e.g., into the page by spindles as described herein) each of the ears on the stalk strike one or more of the strike plates 304 and generate a force measured by the contact instruments 300. The force is measured as one or more of an impact (a count), a variable measured force (e.g., the force corresponds to the size of the ear) or both. The measured force is one example of the one or more crop characteristics measured by the reaping yield instruments 204 (shown in FIG. 2A). The strike plate 304 is in one example a protective plate provided over top of the contact instrument 300. Contact between ears of the cornstalk and the strike plate 304 is transmitted through the strike plate 304 to the contact instrument 300.

Figure 3D:
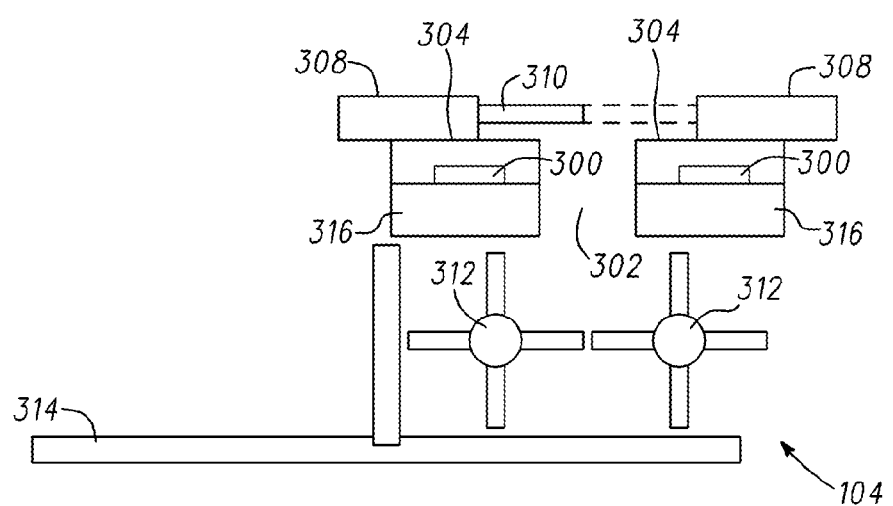
FIG. 3D is a front schematic view of the row section of FIG. 3A.
Figure 3B:
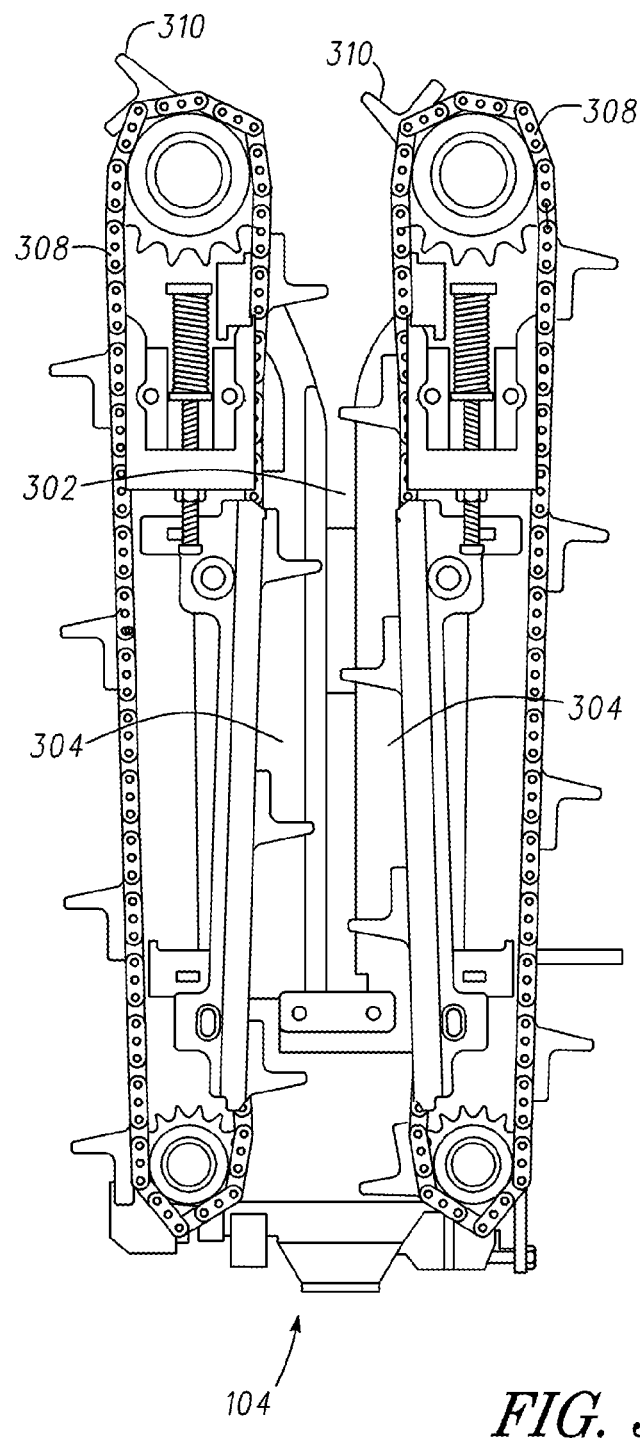
FIG. 3B is a top view of the row section of FIG. 3A including one example of a reaping yield instrument.
Figure 3C:
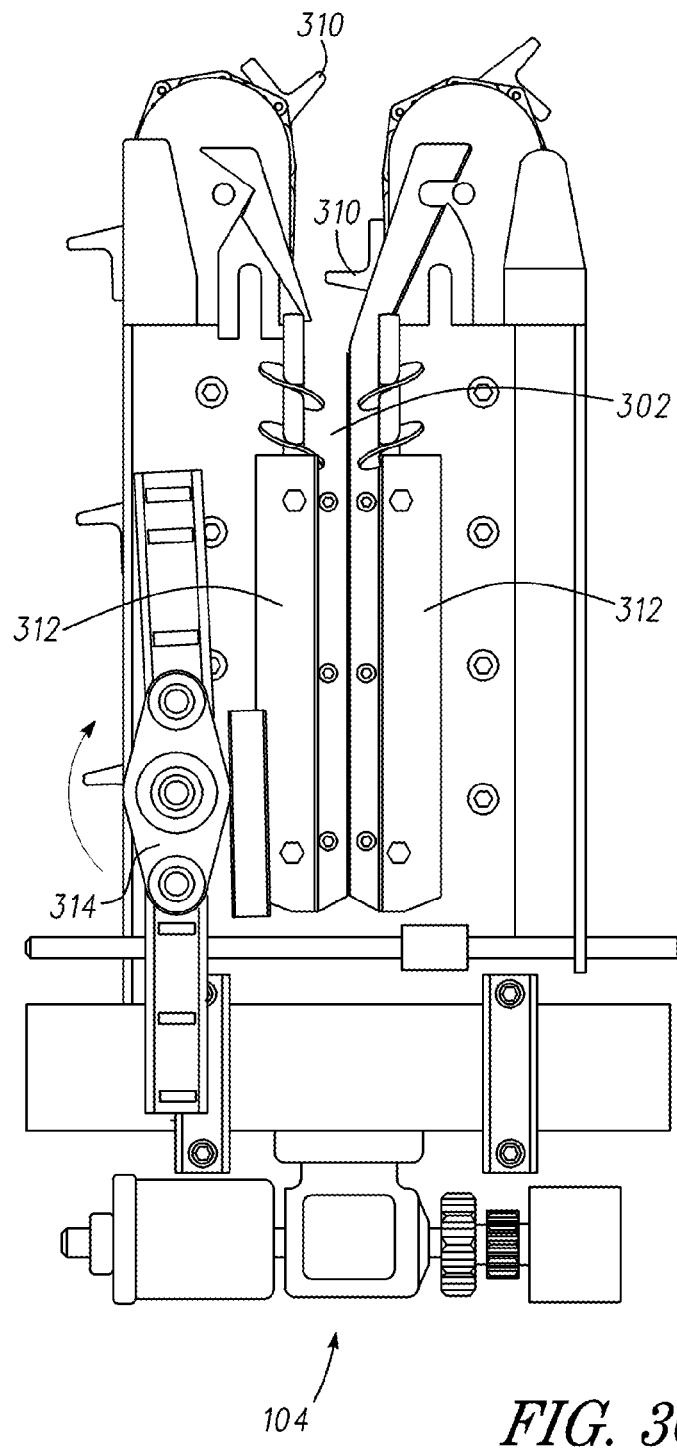
FIG. 3C is a bottom view of the row section of FIG. 3A.

FIGS. 3B and 3C show top and bottom views, respectively, of one example of a row section 104. Referring first to FIG. 3B, the row section 104 is shown with dual chain assemblies 308 provided at the sides of the section gap 302. The chain assemblies 308 include chain teeth 310, for instance interdigitated chain teeth 310, that extend from the chains pull a plant, such as a corn stalk, into the section gap 302 for further processing (e.g., removal of ears of corn from the stalk). As further shown in FIG. 3B, the strike plates 304 are provided to the sides of the section gap 302 and between the chain assemblies 308. The strike plates 304 provide a tapered opening for the section gap 302 to accordingly guide the plants therein.

FIG. 3C shows the row section 104 in a bottom view. The row section 104 includes one or more spindles 312 provided underneath the section gap 302. The spindles 312 cooperate to pinch the cornstalk and draw the cornstalk through the section gap 302 as the cornstalk moves from a first position near the opening of the section gap 302 to a second position closer to the end of the section gap 302. The spindles 312 rotate relative to the remainder of the row section 104 to accordingly draw the stalk downward through the section gap 302 while at the same time pinching the stalk between individual blades or elements of the spindle 312 to facilitate cutting of the stalk into multiple pieces with the chopping blade 314. As shown in FIG. 3C the chopping blade 314 rotates relative to the spindles 312 and cuts stalks provided in the section gap 302 that are pinched by the spindles 312.

In operation, as the harvester 100 moves through a field for instance down a plurality of crop rows corresponding to the number of row sections 104 of the harvester head 102 stalks of corn are received within the section gap 302 of each of the row sections 104. The chain teeth 310 of the chain assemblies 308 rotate in an incoming fashion relative to the section gap 302 and accordingly engage with the corn stalks and draw the stalks into the section gap 302. As the corn stalks are drawn into the section gap 302 the spindles 312 the stalks downwardly through the section gap for instance out of the page as shown in FIG. 3C and into the page as shown in FIG. 3B. The spindles 312 optionally pinch the stalk as it is pulled through and allow for chopping by the chopping blade 314 to cut the stalk into a plurality of pieces for deposition in the field. As discussed herein, the pulling of the stalks pulls the ears of corn against the strike plates 304 and the contact instruments 300 register one or more of the impact or the quantified force of impact.

FIG. 3D shows a schematic front view of one example of the row section 104. In the example the chain assemblies 308 are provided above the contact instruments 300. As previously described herein, in one example the contact instrument 300 is covered by the strike plate 304. The contact instrument 300 includes but is not limited to one or more load cells, piezo elements, magnetic sensors or the like. Impacting the strike plates 304 (e.g., with the crop such as ears of corn) generates a measurable signal, current or voltage that corresponds to one or more crop characteristics (e.g., yield per ear, counting of the number of ears on the stalk, a combination of both or the like). As the stalk is drawn downwardly the ears strike the strike plates 304 (and the force is counted, measured, or both) and are separated from the stalk. The spindles 312 pinch the stalk and allow for the chopping blade 314 to cut the stalk into multiple pieces.

The contact instrument 300 is an example of the reaping yield instrument 204 described herein and measures contact for used with the reaping instrument controller 202. In another example, the contact instrument 300 measures one or more crop characteristics (related to yield) including, but not limited to, counting of crops such as ears of corn impacting the instrument 300, the quantity of force at contact, length of contact or the like. In one example the contact instrument 300 measures a combination of these characteristics and accordingly transmits values corresponding to these measurements to the reaping instrument controller 202. As discussed herein, the reaping instrument controller 202 uses the measured values (e.g., $V_1$, $V_2$, $V_3$, $V_4, V_n$) as the measured crop characteristics used to generate a consolidated characteristic value such as $CV_n$ as previously described herein.

In another example, the measured values of the reaping yield instrument (including the contact instrument, imaging instruments or the like) is used directly to generate and apportion yield values to the sections of the harvester head without a yield monitor (e.g., monitor 206). For instance, the corn ear counts of each section are measured by the reaping yield instruments 204. The reaping instrument controller 202 equates each ear counted to a yield value (such as a portion of a bushel). Accordingly, the ear counts for each section of the harvester head directly result in a variable yields ($VYP_1$, $VYP_2$, $VYP_3$, $VYP_4$, $VYP_n$). In another example, the reaping yield instruments 204 measure one or more of the force of the contact or length of contact. The reaping instrument controller 202 modifies the yield for each counted ear of corn based on the force of the contact, length of contact or both. For instance, the yield of an ear of corn is proportionately increased for one or more of relatively higher impact forces and contact lengths, and similarly proportionately decreased with lesser measured forces and contact lengths. Accordingly, the reaping based yield monitor system 200 (shown in FIG. 2A) is used in a standalone fashion with the reaping yield instruments 204 and the reaping instrument controller 202 to determine yield values for each of a plurality of sections of the harvester header 102. Because the yield values are determined directly with the reaping yield instruments at the time of reaping the yield values are automatically indexed to the sections of the harvester head 102 and the corresponding portions of a field map (e.g., without needing to account for a time delay).

Figure 4:
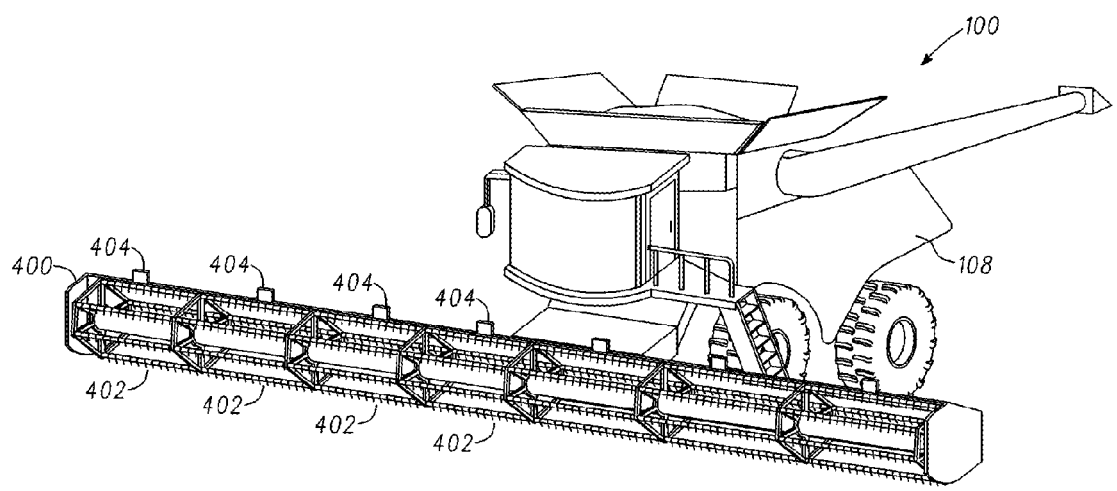
FIG. 4 is a top view of another harvester head including another example of reaping yield instruments.

FIG. 4 shows another example of the harvester 100. In the example shown the harvester 100 includes components similar to at least some of the components previously shown for the harvester 100 provided in FIG. 1. For instance, the harvester 100 includes a grain bin 108 and a harvester head 401. In the example shown in FIG. 4, the harvester head 401 is a grain based harvester head configured to thresh and winnow a grain crop, for instance wheat, soy beans, cotton or the like. As further shown in FIG. 4 the grain harvester head 400 includes a plurality of sections 402 spaced along the harvester head 400.

A plurality of reaping yield instruments 404 are associated with each of the sections 402. The reaping yield instruments 404 measure one or more crop characteristics of the harvested crop (volume, flow rate of the crop through the sections or the like) as it is harvested with the harvester head 400. The reaping yield instruments 404 are in communication with the reaping based yield monitor assembly 200 including the reaping instrument controller 202 shown in FIG. 2A. The reaping yield instruments 404 cooperate with the reaping instrument controller 202 and the overall reaping based yield monitor assembly 200 to measure one or more crop characteristics of the crop as it is harvested with the harvester head 400 and apportion yield (e.g., yield generated by the yield monitor 206 in communication with yield instruments 208). The reaping yield instruments 404 facilitate the apportionment of the variable yield generated by the yield monitor 206 across the harvester head 400. That is to say, the reaping based yield monitor assembly 200 (including in this example the reaping yield instruments 404) provides variable yield portions ($VYP_1$, $VYP_2$, $VYP_3$, $VYP_4$, $VYP_n$) to each of the corresponding sections across the harvester head 400. In this example the resolution provided by the reaping based yield monitor assembly 200 corresponds to each of the sections 402 of the harvester head 400.

Although FIG. 4 shows one example with a plurality of reaping yield instruments 404 distributed along the harvester head 400, in another example the reaping yield instruments 404 are consolidated into a single or fewer instruments 404 than those shown in FIG. 4. For instance, an imaging instrument is provided in the cab of the harvester 100, at a position above or along the harvester head 400, or the like and directed into the sections 402 of the harvester head 400. Imaging or video interpretation modules (including algorithms and the like) interpret the images or video taken of the harvester head 400 while harvesting a crop to provide a corresponding series of measurements for each of the sections 402 of the harvester head 400. The measurements for the one or more crop characteristics are used by the reaping based yield monitor assembly 200 in a manner similar to the manner previously described herein. For instance, the measured values are conveyed to the reaping instrument controller 202 and used by the apportionment module 212 to match the measured values with the corresponding variable yield value generated by the yield monitor 206 for apportionment of the variable yield value across the plurality of sections 402. In one example the reaping yield instruments 404 shown in FIG. 4 include but are not limited to one or more imaging sensors such as infrared (IR), optical, video or ultrasound instruments.

Referring now to FIGS. 5A and 5B, two examples of field maps 500, 504 are provided in each of the respective figures. Referring first to FIG. 5A, one example of a partially completed field map 500 is provided with a harvester such as the harvester 100 positioned at two locations (and times) relative to a single swath or pass of the harvester through a field. The example shown in FIG. 5A provides one example of section based resolution provided with the reaping based yield monitor assembly 200 described herein. As shown in FIG. 5A, the harvester 100 is shown at two positions a position corresponding to a first time ($t_1$) and a second later time ($t_2$). The harvester head 102 of the harvester 100 accordingly harvests crops and measures one or more crop characteristics between at least the two locations with the reaping yield instruments 204 (see FIG. 2A). In the example shown in FIG. 5A at $t_2$ the harvester 100 has passed the harvested crops originally harvested at time $t_1$ and accordingly generates a yield value $YV_1$ with the yield monitor 206 in communication with the yield instruments 208 (downstream from the harvester head 102). As further shown in FIG. 5A, the harvester 100 at the two times $t_1$ and $t_2$ is shown at different positions corresponding to a distance offset 502 (also shown in FIG. 5B).

As previously described herein, in one example the reaping based yield monitor assembly 200 includes an apportionment module 212. In one example the apportionment module 212 (or the reaping instrument controller 202 itself) includes one or more modules or elements configured to apportion the variable yield value $YV_1$, determined with the yield monitor 206 and the yield instruments 208, across a plurality of sections of the harvester head 102 (e.g., as $VYP_1$, $VYP_2$, $VYP_3$, $VYP_4$, $VYP_n$). For instance, as previously discussed herein the apportionment module 212 includes a characteristic value module 214 configured to provide ongoing consolidated values $CV_n$ corresponding to grouped (by time) measured values of crop characteristics taken by the reaping yield instruments 204. The ongoing consolidated yield values $CV_n$ are compared, for instance at the comparator 216, with the later determined variable yield values generated by the yield monitor 206. Based on the comparison the matching module 218 matches the variable yield (e.g., $YV_1$) to the appropriate ongoing consolidated value (e.g., $CV_1$) and thereby provides an association between the corresponding values measured with each of the reaping yield instruments 204 and the variable yield value determined with the yield monitor 206. An assignment module 220 thereafter proportionately divides the assigned variable yield $YV_1$ across the plurality of row sections, such as the row sections 104, according to each of the measured values for the crop characteristics taken by each of the corresponding reaping yield instruments 204 (e.g., $V_1$, $V_2$, $V_3$, $V_4$, $V_n$). As shown in FIG. 5A the variable yield portions (e.g., $VYP_{1-8}$) are provided in a distributed fashion across the harvester head and accordingly provide resolution for the variable yield across the swath of the harvester 100.

Additionally, with the association of the variable yield value $YV_1$ to the earlier measured values of the crop characteristics with the reaping yield instruments 204 the variable yield is apportioned and also indexed to a portion of the field corresponding to sections of the harvester head (shown as plurality of cells on the field map 500) while the harvester 100 is positioned at the initial position ($t_1$) where the crops were harvested as shown in FIG. 5A. That is to say, by matching the variable yield value $YV_1$ to the ongoing consolidated value $CV_1$ (generated by the characteristic value module 214) the variable yield is accurately indexed to the corresponding portion of the field and field map 500 from which the harvested crop that generated the variable yield value was harvested. Accordingly, the variable yield value $YV_1$ is not errantly offset according to the offset 502.

Another example of a field map 504 is provided in FIG. 5B. In this example a harvester, such as the harvester 100, without the reaping based yield monitor assembly 200 described herein but including a yield monitor system is provided in the two locations similar to the two locations provided in FIG. 5A. That is to say, the harvester 100 is shown at a first position corresponding to time $t_1$ and a second position corresponding to later time $t_2$. As shown in FIG. 5B, at time $t_1$ the harvester head 102 harvests a crop such as corn, wheat or the like and proceeds to thresh and winnow the crop and eventually deliver it to a grain elevator 110 shown in FIG. 1. The variable yield value is determined with a yield monitor system, for instance at $t_2$ and with the harvester 100 at the location for $t_2$. The difference between times $t_2$ and $t_1$ corresponds to the amount of time the grain takes for processing and movement through the harvester 100 before it is measured by the yield monitor. In this example the yield value ($VY_1$) is indexed to the field map 504 at a location corresponding to the harvester 100 location at time $t_2$ and spaced according to the offset 502. However the crop harvested by the harvester 100 at $t_1$ is actually the crop used to generate the variable yield value ($VY_1$). The example shown in FIG. 5B thereby errantly indexes the variable yield value $VY_1$ to an offset location. Because the harvested crop takes time to move through the harvester 100 and the harvester continues to move through the field, for instance as shown by the offset 502, when the yield value ($YV_1$) is determined the value is indexed at the later location corresponding to the offset 502 and the location of the harvester at time $t_2$. The yield value $VY_1$ is thereby errantly offset at least by the amount 502.

As shown in FIG. 5B and previously discussed above the yield value ($YV_1$) is indexed at a location of the field map 502 different than the harvested crop that actually generates the yield value. For instance, the yield value $YV_1$ is provided at a location spaced by the offset 502 relative to the initial position of the harvester 100 at $t_1$. Additionally, the yield value $YV_1$ is not apportioned across the harvester head or a corresponding portion of the field as provided on the field map 504. Instead, the yield value $YV_1$ is provided as a single value extending across the swath provided by the harvester 100. That is to say, the yield monitor assembly included with the harvester 100 shown in FIG. 5B is unable to provide the enhanced resolution available with the reaping based yield monitor system 200 described herein and graphically plotted in FIG. 5A. Instead, the yield value $YV_1$ is provided as a unitary value extending across the swath provided by the harvester head 102 on the field map 504 without variation called out between one or more of the sections 104.

FIG. 6 shows one example of a method 600 for apportioning yield. In describing the method 600 reference is made to one or more components, features, functions and steps previously described herein. Where convenient, reference is made to the components, features, steps and the like with reference numerals. The reference numerals provided are exemplary and are not exclusive. For instance, components, features, functions, steps and the like described in the method 600 include, but are not limited to, the corresponding numbered elements provided herein, other corresponding features described herein (both numbered and unnumbered) as well as their equivalents.

At 602, the method 600 includes measuring at least one crop characteristic of a harvested crop in each of a plurality of sections 104 of a harvester head 102 with one or more reaping yield instruments coupled with the harvester head 102. Optionally, a harvester head 400, such as a grain harvester head including sections 402 includes one or more reaping yield instruments 404 that measure at least one crop characteristic. In one example, the at least one crop characteristic includes, but is not limited to, a yield related characteristic including volume, flow rate, number of impacts, length of impact, force of impact or the like.

At 604, a variable yield value of the harvested crop is determined. In one example, the variable yield value is an ongoing measured yield measured and output by a yield monitor 206 in cooperation with yield instruments 208. As shown in FIG. 2A, the yield instruments 208 (in contrast to the reaping yield instruments 204) are downstream from the harvester head 102, for instance near the grain elevator 110.

At 606, the variable yield value of the harvested crop is apportioned to each of the sections (e.g., row sections 104 or sections 402) of the plurality of sections of the harvester head (102, 400) based on the at least one crop characteristic measured in each section of the plurality of sections of the harvester head.

Several options for the method 600 follow. In one example, measuring the at least one crop characteristic includes observing the quantity of the harvested crop with the one or more reaping yield instruments 404 in each section 402 of the plurality of sections 402 (see FIG. 4). In another example, observing the quantity of the harvested crop includes one or more of infrared (IR) sensing, optical sensing, or video sensing.

In another example, determining the variable yield value of the harvested crop includes measuring at least another crop characteristic (e.g., volume, weight, moisture content, temperature or the like) of the harvested crop the same as or different from the at least one crop characteristic measured with the one or more reaping yield instruments, such as counted impacts, force of impact, length of contact, volume flow rates or the like.

Apportioning of the variable yield value includes, in another example, determining an ongoing plurality of characteristic values (e.g., $CV_n$), each of the plurality of characteristic values corresponding to a plurality of measurements of the at least one crop characteristic ($V_1$, $V_2$, $V_3$, $V_4$, $V_n$) taken at a time, such as a first time $t_1$, for each of the plurality of sections of the harvester head 102. Apportioning further includes matching the determined variable yield value $YV_2$ (e.g., taken at $t_2$) with a characteristic value ($CV_1$ taken at time $t_2$) of the plurality of characteristic values ($CV_n$ taken at a plurality of times including $t_2$) based on a comparison of the determined variable yield value with the plurality of characteristic values. Apportioning includes (proportionately) dividing the matched and determined variable yield value $YV_2$ between each section of the plurality of sections according to the plurality of measurements of the at least one crop characteristic taken at the time ($V_1$, $V_2$, $V_3$, $V_4$, $V_n$ taken at time $t_1$). As described herein, the variable yield value ($YV_2$) is thereby proportionately divided into variable yield portions, such as $VYP_1$, $VYP_2$, $VYP_3$, $VYP_4$, $VYP_n$ or the like and assigned to the corresponding sections, such as row sections 104 or sections 402 of the harvester heads 102, 400. In another example, the variable yield portions of each of the plurality of sections (104, 402) to portions of a field map 500 corresponding to each of the harvester head sections at the first time (e.g., occupying the same location at time $t_1$). Optionally, the sections of the harvester head include row sections 104 of the harvester head 102 (sections provided between snouts) and the portions of the field map include crop rows. Mapping the variable yield portions includes mapping the variable yield portions to crop rows of the field map 500 corresponding to each of the harvester head row sections 102 at the first time (e.g., the location of the sections 102 on the field at time $t_1$).

The method 600 further includes, in an example, measuring a delay time between the first and second times of the measurements of the crop characteristics and the matched variable yield. Optionally, apportioning the variable yield includes matching the variable yield with measurements of the at least one crop characteristic in each of the plurality of sections of the harvester head 102 (or 400) according to the delay time (e.g., the second time offset by the delay time). Apportioning further includes dividing the variable yield into variable yield portions proportionately based on the measured values of the matched at least one crop characteristic in each section of the plurality of sections, and assigning the variable yield portions across the sections of the plurality of sections.

Figure 7:
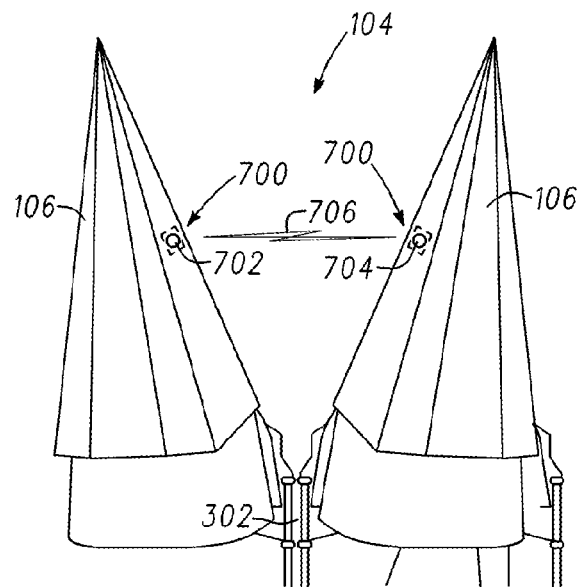
FIG. 7 is a top view of another example of a reaping based yield monitor system.

FIG. 7 shows another example of a row section 104 including a reaping yield instrument. As shown, the row section 104 includes first and second snouts 106 provided to the sides of the section gap 302. A stand count instrument 700 is installed in each of the snouts 106. For instance, in the example the stand count instrument 700 (e.g., another example of a reaping yield instrument) includes a beam emitter 702 installed in one of the snouts 106 and a beam receiver 704 installed in the other snout 106. A beam 706 extends from the beam emitter 702 and is received by the beam receiver 704. As will be described herein, the stand count instrument 700 measures interruptions of the beam 706 received at the beam receiver 704. By measuring the interruptions one or more harvested crop characteristics are measured for the harvested crop including, but not limited to, a stand characteristic such as plant count, rate of plant count, plant width, weed width, leaf width or the like. The measured one or more crop characteristics by the reaping based yield monitor system (described herein, and shown in FIG. 8) to determine one or more yield values including a harvested standing crop value.

In operation, as the harvester 100 including the row section 104 of a plurality of row sections 104 (having corresponding stand count instruments 700 installed in each of the row sections 104) moves through a field and harvests the crop in rows. As the crop is received in the section gap 302 between the snouts 106, the beam 706 of the stand count instrument 700 is broken, for instance by one or more of stalks, leaves, weeds or the like. The reaping instrument controller 202 received measurements of the at least one crop characteristic including a stand characteristic (e.g., a stalk width or the like) and counts the interruptions (width or time of the interruptions, frequency of interruption corresponding to a rate of plant count, or the like) to generate a harvested standing crop value based on the interruptions.

In another example, the at least one crop characteristic, including for instance a harvested standing crop value, is compared with a planting map generated at the beginning of the growing season having a mapped planting density of the crop prior to germination (e.g., a seed planting map). By comparing the counted standing crops and the planted crops yield information including the density of the standing crop relative to the planted crop (seeds) is generated and optionally plotted to a field map or a crop density map as desired.

Referring again to FIG. 7, in one example the stand count instrument 700 includes an infrared (IR) or light beam system that passes the beam 706 from the beam emitter 702 to the beam receiver 704. In another example, an ultrasound generator and receiver are used as the corresponding beam emitter 702 and beam receiver 704. In yet another example, the reaping yield instrument includes, but is not limited to, other examples of reaping yield instruments including, but not limited to, optical, infrared, ultrasonic, camera, video camera or mechanical sensors (including impact sensors such as the impact sensors described herein). Optionally, the sensors are installed in each of the row sections 104, for instance in the snouts 106 or along the section gap 302 in the manner of previously described instruments. The reaping yield instruments measure the one or more crop characteristics including a stand characteristic of the harvested crop. In another example, the reaping yield instruments are installed along the harvester head 102, for instance in an orientation and a direction that provides multiple scan lines for one or more instruments to take measurements in one or more row sections or sections (e.g., of a grade harvester head) to facilitate the observation and measurement of the at least one crop characteristic in each of the sections. In one example a single sensor or a small subset of sensors are directed across the entire width of the harvester head 102 where each of the one or more sensors includes a plurality of scan lines directed toward designated portions of the harvester head 102 to facilitate the measurement of the at least one crop characteristic in each of the sections of the harvester head 102.

Figure 8:
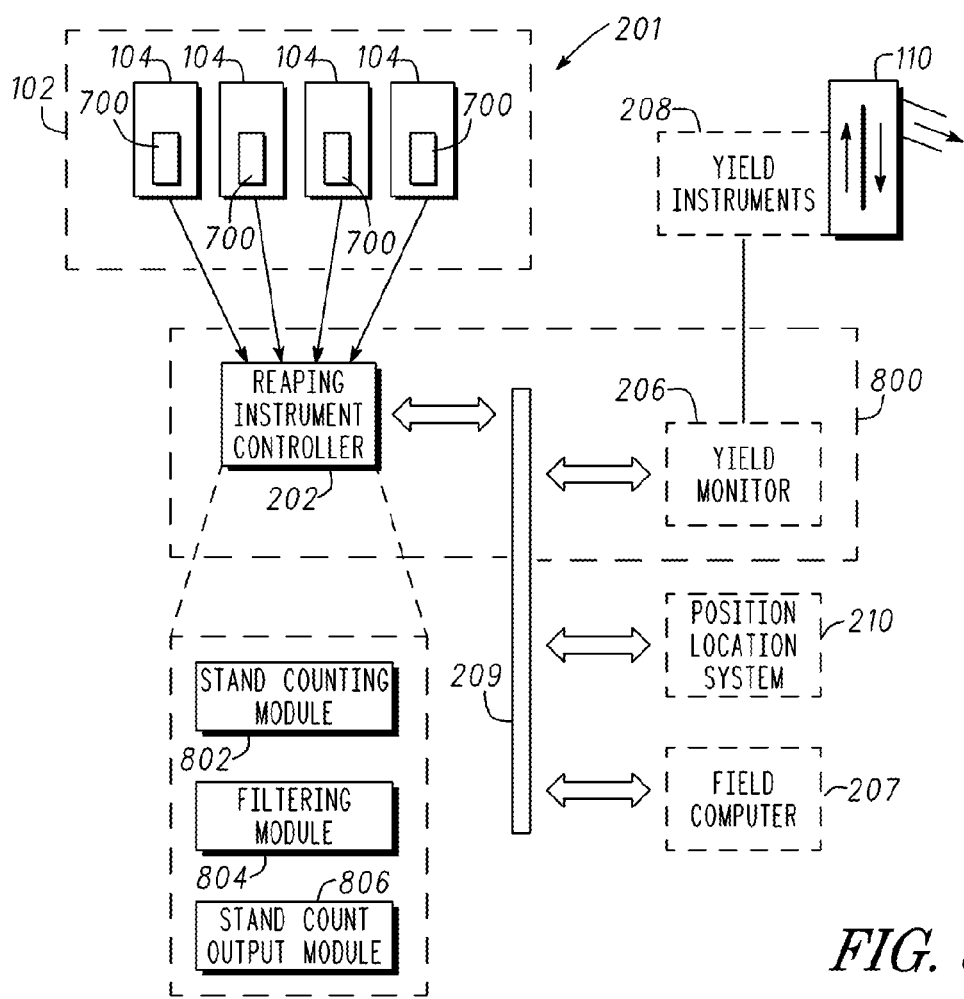
FIG. 8 is a schematic view of one example of the reaping based yield monitor system of FIG. 7.

As previously described herein, the reaping yield instrument such as the stand count instrument 700 and other reaping yield instruments described herein are part of a reaping based yield monitor system 200 shown in FIG. 2A and the reaping based yield monitor system 800 shown in FIG. 8. For the purposes of the discussion herein the harvested standing crop value (e.g., a standing count of a standing crop) within a particular row section or a plurality of row sections 104 corresponds to a yield value generated by the reaping based yield monitor system. In such examples, the harvested standing crop value is another form of yield differing from volumetric and weight based yield values according to the nature of the measurements taken with the reaping yield instruments (e.g., stand count instruments 700) including, but not limited to, plant count, rate of plant count, plant width, weed width, leaf width or the like. In the examples described herein, the standing counts of the standing crop measured by the stand count instrument 700 shown in FIG. 7 are optionally used in combination with yield values, such as volumetric or weight based yield values, to generate refined values for yield including, but not limited to, yield by volume per plant and yield by weight per plant.

FIG. 8 shows another example of a reaping based yield monitor system 800 including for instance the reaping instrument controller 202 and an optional yield monitor 206. As previously described herein the reaping instrument controller 202 is in one example incorporated with the yield monitor 206 (e.g., as a physical add-on component coupled with the yield monitor 206, a software module installed into the yield monitor 206 or the like). In another example, the reaping instrument controller 202 is a standalone component used in cooperation with or separately from the yield monitor 206. Accordingly, the reaping based yield monitor system 800, in another example, includes the reaping instrument controller 202 without a yield monitor 206.

Referring again to FIG. 8, the reaping based yield monitor system 800 includes one or more reaping yield instruments, such as the stand count instruments 700 (previously shown in FIG. 7) shown as a plurality of instruments across the row sections 104. In another example the stand count instruments 700 are consolidated into one or more instruments that scan the entirety or a portion of a harvester head, such as the harvester head 400 shown in FIG. 4 including for instance a grade harvester head. The stand count instruments 700 are in communication with the reaping instrument controller 202 and the reaping instrument controller 202 is configured to interpret measurement data delivered by the stand count instruments 700 and accordingly generate one or more values corresponding to a measured at least one crop characteristic including a stand characteristic of the crop. As previously described herein, in one example the stand characteristic includes but is not limited to a count (counted interruption, length of interruption, time of interruption or the like) associated with a stalk of the plant, weed, leaf of the plant or the like.

As further shown in FIG. 8, in one example the reaping instrument controller 202 is optionally in communication with the yield monitor 206 by way of an interface such as the interface 209. In one example, the interface 209 is a bus such as a CAN bus (controller area network) provided with the harvester 100 to facilitate the communication of a plurality of modules. As further shown in FIG. 8 and previously described herein, in another example the yield monitor 206 is in communication with one or more yield instruments 208 (e.g., associated with the grain elevator 110) at a downstream position relative to the sections of the harvester head including the stand count instruments 700.

As further shown in FIG. 8 the control system 201 optionally includes other components including, but not limited to, a position locating system 210 and a field computer 207. In one example, the position location system 210 includes one or more features such as fiducials, antennas or the like configured to cooperate with a global positioning system (GPS), real time kinematic (RTK) system or the like. Accordingly, the position of the harvester 100 including its movement within a field are measured and tracked by way of the position locating system 210. Optionally, the measured and tracked location of the harvester 100 is used with a field map or planting map stored and available by way of the field computer 207 to plot yield values including the harvested standing crop value generated with the reaping based yield monitor system 800.

As further shown in FIG. 8, in one example a field computer 207 is configured for communication with one or more of the reaping based yield monitor system 800 and the position location system 210 by way of the interface 209. The field computer 207 optionally includes access to a field map, a planting map or the like (e.g., a map with detailed plots, values or the like for previously planted seeds). In another example the field computer 207 provides one or more of automated steering or steering cues to an operator of the harvester 100 to facilitate the guidance of the harvester 100 for accurate harvesting of the planted crop.

Referring again to FIG. 8, in operation the reaping based yield monitor system 800 provides one or more instruments, stand count instruments 700 to measure a stand characteristic (e.g., at least one crop characteristic of a harvested standing crop) and generate a harvested standing crop value corresponding to one or more of a stand count of the harvested standing crop, standing crop density (e.g., relative to planted seeds, area covered by the harvester 100, distance traveled by the harvester 100) yield on a per counted plant basis or the like). As shown in FIG. 8, the one or more stand count instruments 700 for include beam emitters 702 and beam receivers 704. The beams 706 from the beam emitters 702 are broken by the incoming plants and the instruments 700 (e.g., beam receivers 704) measure one or more of interruption of the beam, interruption length, interruption time or the like.

Measured values such as, interruptions, lengths of interruption, interruption time or the like are conveyed to the reaping instrument controller 202 (e.g., by wired or wireless connections such as Bluetooth, radio frequency transmissions or the like) for interpretation by the reaping instrument controller 202 to generate one or more harvested standing crop values based on the measured data. For instance as shown in FIG. 8, in one example the reaping instrument controller 202 includes a stand counting module 802. The stand counting module is configured to interpret one or more of the interruption of the beams, the length or time of interruption of the beams as a corresponding width of one or more of a stalk, leaf, weed or the like. The reaping instrument controller 202 including the stand count module 802 generates and accumulates one or more counts, for instance counts for each of the row sections 104 of the harvester head 102, to thereby count harvested crops as they are harvested with each of the row sections 104. In another example where the harvester head does not include dedicated row sections 104 and instead includes sections corresponding to various portions of the harvester head 400 (e.g., a grain harvester head) each of the stand count instruments 700 is configured to observe a zone or provide a plurality of scan lines directed to zones that measure one or more stand characteristics in each of the respective sections of the harvester head 400.

In another example the stand counts generated by the stand counting module 802 are in one example filtered with a filtering module 804. In one example, the filtering module 804 removes errant results corresponding to weeds, leaves associated with plant stalks (such as leaves of a corn plant) or the like from overall stand counts to provide a refined stand count value closely approximating or equaling the number of standing crops within a particular row (corresponding to a row section 104 or section 402 of the harvester heads 100, 400).

In one example, the filter module 804 refines the stand counts or removes values from interpretation by the stand counting module 802 by comparing the values measured by the one or more of the stand count instruments 700 against a filter threshold. In one example, a filter threshold includes a stalk width (e.g., an average or minimum stalk width for the crop being harvested). The stalk width is equivalent to the minimum stalk width of a corn plant at the time of harvesting. The filter module 804 compares each of the values measured by the stand count instruments 700 against the filter threshold and removes any values less than the filter threshold (e.g., a stalk width). In yet another example, the filter threshold 804 is applied alone or in combination with a filter algorithm. In one example, a filter algorithm ignores counted values that are adjacent to (in time or position) a qualifying value of the at least one crop characteristic (an interruption of a beam for instance) that does satisfy the filter threshold. That is to say, where a stalk includes a plurality of leaves if those leaves otherwise trigger a count with the stand counting module 802 the application of the filter algorithm removes those values because of the nearby association to a qualifying measurement corresponding to a stalk having a stalk width greater than or equal to the filter threshold stalk width.

As further shown in FIG. 8 in another example the reaping instrument controller 202 includes a stand count output module 806. In one example, the stand count output module 806 generates one or more harvested standing crop values (as a type of yield value) based on one or more of the counted harvested standing crop or the filtered measured values of the stand characteristic. For instance, in one example the harvested standing crop value includes a refined stand count for one or more of the sections (such as the row sections 104) based on the application of a filter (filtering module 804) to rough stand counts generated by the stand counting module 802. That is to say, errant measurements such as weeds, leaves or the like are removed from the overall stand count to provide a refined stand count value as the harvested standing crop value. In another example, the harvested standing crop value includes a weed count, such as those measured values of the stand characteristic that are otherwise filtered by the filtering module, and generated as a weed count to provide an indication to the operator of one or more of the frequency, volume or location of weeds within the field. In yet another example, the standing crop value includes the basic output of the standing count module including all measured values of the standing characteristics by the one or more stand count instruments 700 (e.g., unrefined with the filtering module 804).

In other examples, the stand count output module 806 generates one or more other outputs based on the measured values of the stand characteristic received and interpreted by the reaping instrument controller 102. Other possible outputs include, but are not limited to, harvested standing crop value in the form of a standing crop density relative to a distance traveled by the harvester 100 (e.g., density is provided in units of plants per foot, meter or the like). In another example, the harvested standing crop value is an area based density corresponding to the area covered by the harvester head 102, 104 during the harvesting operation (provided in units of plants per square feet, square meters or the like). Where the field computer 207 includes access to a planting map providing detailed information on one or more of the density of the planted crop (e.g., seeds), the actual indexed locations of the planted seeds or the like the stand count output module is in one example configured to provide a stand count density of the standing crop relative to the planted crop (e.g., harvested standing plants per seed planted). Accordingly with one or more of the outputs described herein, the operator is able to determine by way of the harvested standing crop value the ratio of standing crops harvested relative to the number of seeds planted originally. Accordingly with one or more of the outputs described herein the operator is able to quantitatively review performance of planted seeds (e.g., one or more hybrids) through a comparison of the harvested standing crop relative to the planted crop. The operator may then quantitatively determine which of a plurality of planted hybrids provides the best germination and harvest potential and will make enhanced decisions regarding planting of hybrids and husbandry of the crop (watering, agricultural product application or the like) in the next season.

In another example, where the reaping instrument controller 202 is incorporated with or in communication with a yield monitor 206 the harvested standing crop value generated with the stand count output module is used to provide one or more refined yield values based on volumetric or weight based yield determined with the yield instruments 208 in cooperation with the yield monitor 206. In one example, where the yield monitor 206 is configured to determine the yield for one or more sections discretely or collectively (as described herein and shown in FIG. 2A), a portion of the field such as a zone, or the like the yield values of interest are divided by the harvested plants (within the section or zone) counted with the reaping instruments controller 202 and the stand count instruments 700 to determine one or more yield values including for instance yield as a function of weight per harvested plant or yield as a function of volume per harvested plant. Further, with the reaping based yield monitor system 200 described herein, the resolution and indexing of high resolution yield values (volume or weight per plant) is possible for each section (crop row) of a field. Accordingly, the operator readily determines the yield value for a particular type of crop for instance one or more differing types of hybrids on a per plant basis. The operator may then quantitatively determine which of a plurality of hybrids provides the most yield per plant and is thereby able to make enhanced decisions regarding planting of hybrids and husbandry of the crop (watering, agricultural product application or the like) in the next season.

In still another example the field computer 207 includes a planting map that plots the seeds planted at the beginning of the season for a particular crop, such as corn (or a plurality of hybrids of a crop). In such an example, the reaping instrument controller 202 is in communication with the field computer 207. The stand count output module 806 communicates with the field computer 207 to compare the number of counted and harvested standing crops relative to the planted seeds and determine the plant density of the standing crops relative to the planted seeds provided on the plant map. In another example the stand count output module generates a harvested standing crop value as a plotted map and includes not only the planted seeds but also the counts of the harvested standing crop relative to the planted seeds. In such an example (shown for instance in FIG. 9B) the reaping based yield monitor system 800 provides a plot of the actual harvested standing crop relative to the originally planted seeds. The operator readily determines which parts of a field or zones of a field have particular difficulty or ability to grow a crop. In another example, based on the plotting together of the harvested standing crop values and the planted seeds (e.g., on a field map) or comparison of numbers of the harvested standing crop relative to planted seeds the operator may qualitatively or quantitatively ascertain the overall germination rate and viability of a particular hybrid or plant type within a field.

Figure 9A:
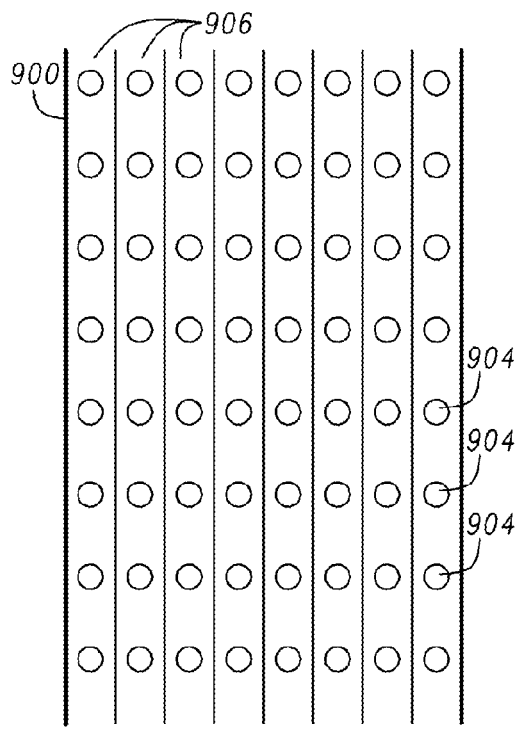
FIG. 9A is a schematic diagram of one example of a planting map including indexed planted crops.

FIG. 9A shows one example of a planting map 900, such as the planting map previously described in regard to the field computer 207. As shown, the planting map 900 provides a graphical representation of each of the planted seeds 904 in a plurality of crop rows 906. In another example, the planting map 900 provides the number of planted seeds 904 by way of density measurements provided across rows, crop rows, zones or the like of a field.

Figure 9B:
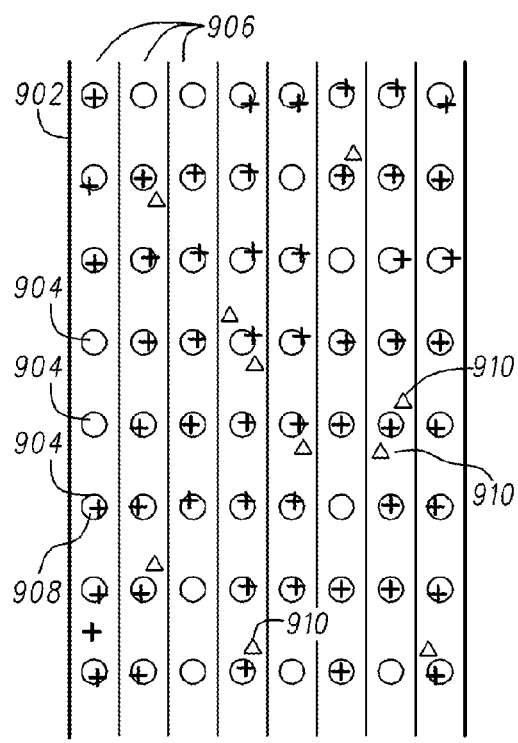
FIG. 9B is a schematic diagram of one example of a consolidated planted and standing crop map.

FIG. 9B shows another example of a map, in this case a consolidated planting and standing crop density map 902 including the original data presented by the planting map 900 as well as values corresponding to the measured values of the stand characteristic by the one or more reaping yield instruments such as the stand count instruments 700 shown in FIG. 8. The harvested standing crops 908 are shown by stars. In a similar manner filtered measured values 910 (e.g., filtered with the filtering module 804) are indicated with triangular shapes. As shown in FIG. 9B, not all of the planted seeds 904 germinate or are harvested. Similarly, the filtered measured values 910 include, but are not limited to, measurements of the stand characteristics corresponding to leaves in a first case where the triangular elements are shown near a harvested standing crop 908 or weeds where the filtered measured values 910 and corresponding triangular elements are adjacent to planted seeds 904 that are not otherwise harvested during the harvest process (or are remote from other harvested standing crops 908) by the harvester 100.

Referring again to FIG. 9B, the consolidated planting and standing crop density map 902 provides a graphical representation providing consolidated plots of both of the planted and standing crops as they were originally planted and later harvested (and counted). The graphical plot provides a representation for the operator to use for qualitative review of planting and growing characteristics of one or more particular plants for instance one or more hybrids of a particular plant (a first and second hybrid of corn for instance). In another example, the map 902 allows the operator to note various features of the field including, but not limited to, exposed regions, elevated regions, depressed regions or the like that may have difficulty or provide enhanced growing conditions for a crop. Additionally, the resolution provided by the consolidated planting and standing crop density map 902 corresponds to the resolution of the stand count instruments 700. For instance, in the example shown in FIG. 8 the stand count instruments 700 are assigned to each of the row sections 104 of a harvester such as the harvester 100. In another example, the stand count instrument 700 is a single or lesser number of instruments relative to a plurality of sections of a harvester head such as the harvester head 400 (e.g., a grain or cotton harvester head). In such an example the stand count instrument 700 includes a plurality of scan lines or sensors that are directed toward various portions of the harvester head 400 to accordingly sense the at least one crop characteristic in each of the sections of the harvester head 400. In either case the resolution of the stand count instruments 700 provide increased resolution across the entire swath of a harvester head such as the harvester heads 102, 400 to thereby provide enhanced section based resolution (as shown in FIG. 9B) for the harvested standing crop 908. Accordingly, the operator is able to see by the crop rows 906 a representation of the standing crop 908 relative to the planted seeds 904 to qualitatively review, with increased resolution, the behavior of the crop relative to its planting.

Although FIGS. 9A and 9B provide a graphical or pictorial representation of the planted seeds 904, the standing crop 908 as well as filtered measured values 910 are, in another example, provided indexed to the consolidated planted and standing crop density map and the planting map 900 as numerical representations. For instance one or more counted standing crops 908 in a particular zone (a collection of crop rows or a region of a field) relative to the planted seeds 904 for the same zone are provided in a numerical format discussed herein (e.g., a harvested crop stand count relative to the number of planted seeds for the zone). With a pictorial representation or a numerical representation the stand count output module 806 by itself or in cooperation with the yield monitor 206 is able to generate one or more harvested standing crop values based on the counts of the standing crop 908 and plot or list the values for later analysis.

Figure 10:
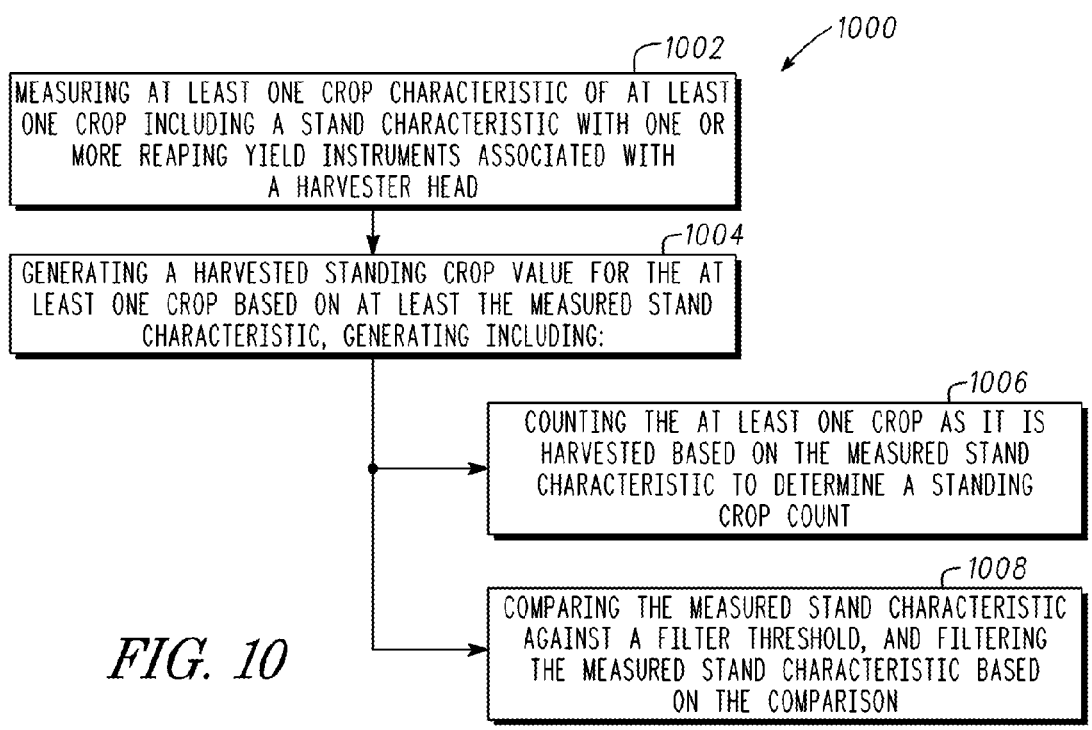
FIG. 10 is a block diagram of one example of a method for counting standing crops.

FIG. 10 shows one example of a method 1000 for measuring reap based yield. In describing the method 1000 reference is made to one or more components, features, functions and steps previously described herein. Where convenient, reference is made to the components, features, steps and the like with reference numerals. The reference numerals provided are exemplary and are not exclusive. For instance, components, features, functions, steps and the like described in the method 1000 include, but are not limited to, the corresponding numbered elements provided herein, other corresponding features described herein (both numbered and unnumbered) as well as their equivalents.

At 1002, at least one crop characteristic of at least one crop is measured. The at least one crop characteristic includes a stand characteristic such as stalk width, a stalk count or the like. The at least one crop characteristic is measured with one or more reaping yield instruments 700 associated with a harvester head 102 (see FIG. 8). Optionally, the one or more reaping yield instruments 700 (e.g., stand count instruments) each include a beam emitter 702 that generates a beam 706, and a beam receiver 704 that senses the beam and senses interruptions of the beam 706. In another example, the one or more reaping yield instruments 700 one or more of imaging, optical or video sensors (e.g., infrared, camera, video camera) or the like configured to measure and count a crop as it is harvested.

At 1004, a harvested standing crop value is generated for the at least one crop based on at least the measured stand characteristic. The harvested standing crop value is a type of yield value including, but not limited to, a harvested plant count, plant count as function of distance traveled or area covered by the harvester 100, yield (volumetric or weight) per harvested plant or the like. Generating the harvested standing crop value includes counting the at least one crop as it is harvested based on the measured stand characteristic to determine a standing crop count. For instance, interruptions, length of interruption (e.g., time of interruption) or the like are measured and counted with the stand count instruments 700 and the reaping instrument controller 202. In another example, generating the harvested standing crop value includes comparing the measured stand characteristic, such as a stalk width measured (e.g., a beam interruption length) against a filter threshold, such as a stalk width threshold, and filtering the measured stand characteristic based on the comparison. For instance, measurements below a stalk width threshold are ignored or separately counted (e.g., as a weed count).

Several options for the method 1000 follow. In one example, one or more reaping yield instruments includes a plurality of reaping yield instruments, each of the reaping yield instruments (e.g., stand count instruments) associated with at least one section of a plurality of sections 104, 402 of a harvester head 102, 400. Counting the at least one crop includes counting the at least one crop in each section of the plurality of sections with a respective reaping yield instrument 700 of the plurality of reaping yield instruments 700. As discussed herein, the corresponding counts for each section provide resolution on a section (e.g., crop row) basis.

In another example, generating the harvested standing crop values includes dividing the standing crop count (e.g., with section based resolution) by one or more of the distance traveled or area covered by one or more sections of a plurality of sections of a harvester head to generate a standing crop count per unit of distance or per unit of area. Where the stand crop counts are indexed according to crop row (e.g., row sections 104) the resulting standing crop values (crop count per unit distance or area) have the same enhanced (section based) resolution relative to a lesser resolution corresponding to the width of a harvester head.

In yet another example, the method 1000 includes determining one or more of a volumetric or weight yield value of the at least one crop (e.g., with the yield monitor 206 and yield instruments 208). Generating the harvested standing crop value for the at least one crop includes dividing one or more of the volumetric or weight yield value by the standing crop count, and the harvested standing crop value includes a volumetric or weight yield per plant value. Optionally, where the yield values and stand counts are apportioned (see discussion herein and exemplary FIGS. 2A, B) by sections, the harvested standing crop value is in one example apportioned by sections (e.g., sections corresponding to the row sections 104 and 402 of FIGS. 1 and 4, respectively). Accordingly resolution of yield per plant per section is achieved with section based resolution of yield values and harvested plant counts.

In still another example, generating the harvested standing crop value for the at least one crop includes comparing the standing crop count against a planted crop count (e.g., planted seeds indexed to a planting map 900 or tabulated and stored numerically). The harvested standing crop count based on the standing crop count and the planted crop count (planted seed count) is represented as a crop density map based on the comparison of the standing crop count relative to the planted crop count with either of plotted elements indicative of planting and harvesting (see FIG. 9B) or indexed values of harvested standing crop counts relative planted crop counts.

Optionally, measuring the at least one crop characteristic and generating the harvested standing crop value is conducted for first and second crops (e.g., first and second hybrids) for evaluation of performance of the first and second crops. Measuring the at least one crop characteristic of the first and second crops includes measuring stand characteristics with one or more of the reaping yield instruments 700, and generating first and second harvested standing crop values for the respective first and second crops (e.g., respective stand counts) based on at least the measured stand characteristics.

In one example, generating the first and second harvested standing crop values includes counting the first crop as it is harvested based on the measured stand characteristic of the first crop to determine a first standing crop count and counting the second crop as it is harvested based on the measured stand characteristic of the second crop to determine a second standing crop count. A first crop density is identified including comparing the first standing crop count to a first planted crop count. A second crop density is identified including comparing the second standing crop count to a second planted crop count. The first and second crop densities are compared to evaluate the growth and germination of the first and second crops (e.g., to facilitate purchasing and planning for planting and husbandry in the next season).

In another example, generating the first and second harvested standing crop values includes counting the first crop as it is harvested based on the measured stand characteristic of the first crop to determine the first standing crop count, and counting the second crop as it is harvested based on the measured stand characteristic of the second crop to determine a second standing crop count. First and second volumetric or weight yield values of each of the first and second crops are determined, respectively. The reaping based yield monitor system 200 described herein, optionally including apportionment of variable yield values, is used to determine the first and second volumetric or weight yield values. The first volumetric or weight yield values are divided by the first standing crop count to provide a first harvested standing crop value including a first volumetric or weight yield per plant value. The second volumetric or weight yield values are divided by the second standing crop count to provide a second harvested standing crop value including a second volumetric or weight yield per plant value. In a similar manner to the first and second crop densities the first and second yield per plant values are compared to evaluate the respective yields of the first and second crops on a per plant basis (e.g., to facilitate purchasing and planning for planting and husbandry in the next season).

Various Notes & Examples

Example 1 can include subject matter, such as can include a reaping based yield monitor system comprising: one or more reaping yield instruments configured for coupling with a harvester head, the one or more reaping yield instruments measure at least one crop characteristic of a harvested crop in each of a plurality of sections of the harvester head; and a yield monitor assembly in communication with the one or more reaping yield instruments, the yield monitor assembly includes: a yield monitor configured to determine a variable yield of the harvested crop, and an apportionment module configured to apportion the variable yield of the harvested crop to each of the sections of the harvester head based on the at least one crop characteristic measured in each of the plurality of sections of the harvester head.

Example 2 can include, or can optionally be combined with the subject matter of Example 1, to optionally include wherein the plurality of sections of the harvester head include a plurality of row sections of the harvester head.

Example 3 can include, or can optionally be combined with the subject matter of one or any combination of Examples 1 or 2 to optionally include wherein the one or more reaping yield instruments includes a plurality of dedicated reaping yield instruments each configured for association with a respective row section of the plurality of row sections, and each of the dedicated reaping yield instruments is configured to measure the at least one crop characteristic at the associated respective row section.

Example 4 can include, or can optionally be combined with the subject matter of one or any combination of Examples 1-3 to optionally include wherein the one or more reaping yield instruments includes a contact instrument at each of the plurality of row sections.

Example 5 can include, or can optionally be combined with the subject matter of one or any combination of Examples 1-4 to optionally include wherein the one or more reaping yield instruments include one or more imaging instruments.

Example 6 can include, or can optionally be combined with the subject matter of Examples 1-5 to optionally include wherein the one or more imaging instruments includes one or more of infrared (IR), optical, or video instruments.

Example 7 can include, or can optionally be combined with the subject matter of Examples 1-6 to optionally include one or more yield instruments in communication with the yield monitor, the one or more yield instruments are different than the one or more reaping yield instruments, the one or more yield instruments are configured to measure at least another crop characteristic the same as or different from the at least one crop characteristic, and the yield monitor determines the variable yield of the harvested crop based on the measured at least another crop characteristic.

Example 8 can include, or can optionally be combined with the subject matter of Examples 1-7 to optionally include wherein the one or more yield instruments are configured for coupling with a grain elevator of the harvester, and the one or more reaping yield instruments are configured for coupling with the harvester head upstream from the grain elevator and the one or more yield instruments.

Example 9 can include, or can optionally be combined with the subject matter of Examples 1-8 to optionally include wherein the apportionment module includes a matching module configured to match the determined variable yield taken at a second time with at least one corresponding measurement of the at least one crop characteristic of the harvested crop measured with the one or more reaping yield instruments and taken at an earlier first time relative to the second time.

Example 10 can include, or can optionally be combined with the subject matter of Examples 1-9 to optionally include wherein the one or more reaping yield instruments includes a plurality of reaping yield instruments, and the apportionment module includes: a characteristic value module configured to store a plurality of ongoing consolidated values, each ongoing consolidated value corresponding to measurements of the crop characteristic measured with the plurality of reaping yield instruments taken at a first time for each of the plurality of sections of the harvester head, a comparator configured to compare the determined variable yield against the plurality of ongoing consolidated values, the determined variable yield determined at a second later time relative to the first time, a matching module configured to match the determined variable yield with an ongoing consolidated value of the plurality of ongoing consolidated values based on the comparison, and an assignment module configured to divide the matched determined variable yield into variable yield portions between each section of the plurality of sections of the harvester head according to the measurements of the at least one crop characteristic measured with the plurality of reaping yield instruments.

Example 11 can include, or can optionally be combined with the subject matter of Examples 1-10 to optionally include wherein the apportionment module includes a delay module configured to measure a delay time between the first and second times of the measurements of the crop characteristics and the determined variable yield.

Example 12 can include, or can optionally be combined with the subject matter of Examples 1-11 to optionally include wherein the apportionment module includes an indexing module in communication with a field map, and the indexing module is configured to map the variable yield portions of each of the plurality of sections to portions of the field map corresponding to each of the harvester head sections at the first time.

Example 13 can include, or can optionally be combined with the subject matter of Examples 1-12 to optionally include wherein the sections of the harvester head include row sections of the harvester head, and the portions of the field map include crop rows, and the indexing module is configured to map the variable yield portions of each of the plurality of row sections to the crop rows of the field map corresponding to each of the harvester head row sections at the first time.

Example 14 can include, or can optionally be combined with the subject matter of Examples 1-13 to optionally include wherein the one or more harvesting yield instruments includes a contact instrument coupled along at least one deck plate of a harvester row section.

Example 15 can include, or can optionally be combined with the subject matter of Examples 1-14 to optionally include wherein the contact instrument includes a load cell system.

Example 16 can include, or can optionally be combined with the subject matter of Examples 1-15 to optionally include wherein the contact instrument includes a protective plate covering the load cell system.

Example 17 can include, or can optionally be combined with the subject matter of Examples 1-16 to optionally include wherein the one or more reaping yield instruments includes a plurality of reaping yield instruments, and the apportionment module includes: a matching module configured to match the determined variable yield with measurements of the at least one crop characteristic in each of the plurality of sections of the harvester head according to a delay time between the measuring of the at least one crop characteristic and determining of the variable yield, and an assignment module configured to divide the matched determined variable yield into variable yield portions between each of the sections of the plurality of sections according to the measurements of the at least one crop characteristic in each of the plurality of sections with the plurality of reaping yield instruments.

Example 18 can include, or can optionally be combined with the subject matter of Examples 1-17 to optionally include a reaping based yield measuring system comprising: one or more reaping yield instruments configured for coupling with a harvester head, the one or more harvesting yield instruments measure at least one crop characteristic in each of a plurality of sections of the harvester head; a reaping instrument controller in communication with the one or more harvesting yield instruments, the reaping instrument controller configured for communication with a yield monitor; and wherein the reaping instrument controller is configured to apportion a determined variable yield generated by the yield monitor to each of the sections of the plurality of sections according to measurements of the at least one crop characteristic in each of the plurality of sections of the harvester head.

Example 19 can include, or can optionally be combined with the subject matter of Examples 1-18 to optionally include a yield monitor in communication with the reaping instrument controller, the yield monitor is configured to determine the variable yield of the harvested crop.

Example 20 can include, or can optionally be combined with the subject matter of Examples 1-19 to optionally include one or more yield instruments in communication with the yield monitor, the one or more yield instruments are different than the one or more reaping yield instruments, the one or more yield instruments are configured to measure at least another crop characteristic the same as or different from the at least one crop characteristic, and the yield monitor determines the variable yield of the harvested crop based on the measured at least another crop characteristic.

Example 21 can include, or can optionally be combined with the subject matter of Examples 1-20 to optionally include wherein the one or more yield instruments are configured for coupling with a grain elevator of the harvester, and the one or more reaping yield instruments are configured for coupling with the harvester head upstream from the grain elevator and the one or more yield instruments.

Example 22 can include, or can optionally be combined with the subject matter of Examples 1-21 to optionally include wherein the plurality of sections of the harvester head include a plurality of row sections of the harvester head.

Example 23 can include, or can optionally be combined with the subject matter of Examples 1-22 to optionally include wherein the one or more reaping yield instruments includes a plurality of dedicated reaping yield instruments each configured for association with corresponding row sections of the plurality of row sections, and each of the dedicated reaping yield instruments is configured to measure the at least one crop characteristic at the respective corresponding row section.

Example 24 can include, or can optionally be combined with the subject matter of Examples 1-23 to optionally include wherein the one or more reaping yield instruments includes a contact instrument configured for positioning at each row section of the plurality of row sections.

Example 25 can include, or can optionally be combined with the subject matter of Examples 1-24 to optionally include wherein the one or more reaping yield instruments include one or more imaging instruments.

Example 26 can include, or can optionally be combined with the subject matter of Examples 1-25 to optionally include wherein the one or more imaging sensors includes one or more of infrared (IR), optical, or video instruments.

Example 27 can include, or can optionally be combined with the subject matter of Examples 1-26 to optionally include wherein the plurality of sections of the harvester head includes a plurality of sections of the harvester head, and the one or more imaging instruments includes a plurality of dedicated imaging instruments each configured for association with respective sections of the plurality of sections of a harvester head to measure the at least one crop characteristic at each of the sections.

Example 28 can include, or can optionally be combined with the subject matter of Examples 1-27 to optionally include wherein the one or more imaging instruments includes a single stream video instrument configured to measure the at least one crop characteristic at each section of the plurality of sections.

Example 29 can include, or can optionally be combined with the subject matter of Examples 1-28 to optionally include wherein the one or more reaping yield instruments include a plurality of reaping yield instruments, and the reaping instrument controller includes: a characteristic value module configured to store a plurality of ongoing consolidated values, each ongoing consolidated value corresponding to measurements of the crop characteristic measured with the plurality of reaping yield instruments taken at a first time for each of the plurality of sections of the harvester head, a comparator configured to compare the determined variable yield against the plurality of ongoing consolidated values, the determined variable yield determined at a second later time relative to the first time, a matching module configured to match the determined variable yield with an ongoing consolidated value of the plurality of ongoing consolidated values based on the comparison, and an assignment module configured to divide the determined variable yield into variable yield portions between each section of the plurality of sections of the harvester head according to the measurements of the at least one crop characteristic measured with the plurality of reaping yield instruments.

Example 30 can include, or can optionally be combined with the subject matter of Examples 1-29 to optionally include wherein the reaping instrument controller includes a delay module configured to measure a delay time between the first and second times of the measurements of the crop characteristics and the determined variable yield.

Example 31 can include, or can optionally be combined with the subject matter of Examples 1-30 to optionally include wherein the reaping instrument controller includes an indexing module in communication with a field map, and the indexing module is configured to map the variable yield portions of each of the plurality of sections to portions of the field map corresponding to each of the harvester head sections at the first time.

Example 32 can include, or can optionally be combined with the subject matter of Examples 1-31 to optionally include wherein the sections of the harvester head include row sections of the harvester head, and the portions of the field include crop rows, and the indexing module is configured to associate the apportioned variable yield of the harvested crop at each of the row sections of the harvester head to the portions of crop rows of the field on a field map corresponding to each location of the row sections of the harvester head based on the determined delay.

Example 33 can include, or can optionally be combined with the subject matter of Examples 1-32 to optionally include wherein the one or more harvesting yield instruments includes a contact instrument coupled along at least one deck plate of a harvester row section.

Example 34 can include, or can optionally be combined with the subject matter of Examples 1-33 to optionally include wherein the contact instrument includes a load cell system.

Example 35 can include, or can optionally be combined with the subject matter of Examples 1-34 to optionally include wherein the contact instrument includes a protective plate covering the load cell system.

Example 36 can include, or can optionally be combined with the subject matter of Examples 1-35 to optionally include wherein the reaping instrument controller includes: a matching module configured to match the determined variable yield with measurements of the at least one crop characteristic in each of the plurality of sections of the harvester head according to a delay time between the measuring of the at least one crop characteristic and determining of the variable yield, and an assignment module is configured to divide the matched determined variable yield into variable yield portions between each of the sections of the plurality of sections according to the measurements of the at least one crop characteristic in each of the plurality of sections with the plurality of reaping yield instruments.

Example 37 can include, or can optionally be combined with the subject matter of Examples 1-36 to optionally include a method for apportioning yield comprising: measuring at least one crop characteristic of a harvested crop in each of a plurality of sections of a harvester head with one or more reaping yield instruments coupled with the harvester head; determining a variable yield of the harvested crop; and apportioning the variable yield of the harvested crop to each of the sections of the plurality of sections of the harvester head based on the at least one crop characteristic measured in each section of the plurality of sections of the harvester head.

Example 38 can include, or can optionally be combined with the subject matter of Examples 1-37 to optionally include wherein measuring the at least one crop characteristic includes measuring the number of contacts made with the one or more reaping yield instruments in each section of the plurality of sections.

Example 39 can include, or can optionally be combined with the subject matter of Examples 1-38 to optionally include wherein the plurality of sections includes a plurality of row sections of a harvester head, and measuring the at least one crop characteristic includes measuring the number of contacts made with the one or more reaping yield instruments in each section of the plurality of row sections.

Example 40 can include, or can optionally be combined with the subject matter of Examples 1-39 to optionally include wherein measuring the at least one crop characteristic includes observing the quantity of the harvested crop with the one or more reaping yield instruments in each section of the plurality of sections.

Example 41 can include, or can optionally be combined with the subject matter of Examples 1-40 to optionally include wherein observing the quantity of the harvested crop includes one or more of infrared (IR) sensing, optical sensing, or video sensing.

Example 42 can include, or can optionally be combined with the subject matter of Examples 1-41 to optionally include wherein determining the variable yield of the harvested crop includes measuring at least another crop characteristic of the harvested crop the same as or different from the at least one crop characteristic with one or more yield instruments, the one or more yield instruments are different from the one or more reaping yield instruments.

Example 43 can include, or can optionally be combined with the subject matter of Examples 1-42 to optionally include wherein apportioning the variable yield of the harvested crop includes: generating an ongoing plurality of characteristic values, each of the plurality of characteristic values corresponding to a plurality of measurements of the at least one crop characteristic taken at a first time for each of the plurality of sections of the harvester head, comparing the variable yield against the plurality of ongoing consolidated values, the variable yield determined at a second later time relative to the first time, matching the variable yield with an ongoing characteristic value of the plurality of characteristic values based on the comparison, and dividing the matched variable yield between each section of the plurality of sections according to the plurality of measurements of the at least one crop characteristic taken at the first time.

Example 44 can include, or can optionally be combined with the subject matter of Examples 1-43 to optionally include measuring a delay time between the first and second times of the measurements of the crop characteristics and the matched variable yield.

Example 45 can include, or can optionally be combined with the subject matter of Examples 1-44 to optionally include mapping the variable yield portions of each of the plurality of sections to portions of a field map corresponding to each of the harvester head sections at the first time.

Example 46 can include, or can optionally be combined with the subject matter of Examples 1-45 to optionally include wherein the sections of the harvester head include row sections of the harvester head, and the portions of the field map include crop rows, and mapping the variable yield portions includes mapping the variable yield portions to crop rows of the field map corresponding to each of the harvester head row sections at the first time.

Example 47 can include, or can optionally be combined with the subject matter of Examples 1-46 to optionally include wherein apportioning the variable yield of the harvested crop includes: matching the variable yield with measurements of the at least one crop characteristic in each of the plurality of sections of the harvester head according to a delay time between the measuring of the at least one crop characteristic and determining of the variable yield, and assigning the variable yield across the sections of the plurality of sections, assigning includes dividing the matched variable yield between each section of the plurality of sections according to the measurements of the at least one crop characteristic in each of the sections of the plurality of sections with the one or more reaping yield instruments.

Example 48 can include, or can optionally be combined with the subject matter of Examples 1-47 to optionally include a reaping based yield monitor system comprising: one or more reaping yield instruments configured for coupling with a harvester head, the one or more reaping yield instruments measure at least one crop characteristic of a harvested standing crop including a stand characteristic; and a reaping instrument controller in communication with the one or more reaping yield instruments, the reaping instrument controller includes: a stand counting module configured to count the harvested standing crop based on measured values of the stand characteristic by the one or more reaping yield instruments, a filtering module configured to compare measured values of the stand characteristic against a filter threshold and filter measured values of the stand characteristic based on the comparison, and a stand count output module configured to output a harvested standing crop value based on one or more of the counted harvested standing crop or the filtered measured values of the stand characteristic.

Example 49 can include, or can optionally be combined with the subject matter of Examples 1-48 to optionally include wherein the one or more reaping yield instruments include a plurality of reaping yield instruments each configured for installation in respective sections of a plurality of sections of the harvester head.

Example 50 can include, or can optionally be combined with the subject matter of Examples 1-49 to optionally include wherein each of the one or more reaping yield instruments includes: a beam emitter configured for installation in a first snout of a section of the harvester head, a beam receiver configured for installation in a second snout of the second the harvester head, and wherein the beam emitter is configured to emit a beam received by the beam receiver.

Example 51 can include, or can optionally be combined with the subject matter of Examples 1-50 to optionally include wherein the stand counting module counts the standing crop based on interruptions of reception of the beam at the beam receiver.

Example 52 can include, or can optionally be combined with the subject matter of Examples 1-51 to optionally include wherein the one or more reaping yield instruments include one or more of optical, infrared, ultrasonic, camera or mechanical sensors.

Example 53 can include, or can optionally be combined with the subject matter of Examples 1-52 to optionally include wherein the one or more reaping yield instruments include scanning arc sensors configured for staggered installation along a grain platform harvesting head.

Example 54 can include, or can optionally be combined with the subject matter of Examples 1-53 to optionally include wherein the stand characteristic includes a stalk width and the filter threshold includes a stalk width threshold, and the filtering module is configured to compare a measured stalk width with the stalk width threshold and filter measured values of stalk width below the stalk width threshold.

Example 55 can include, or can optionally be combined with the subject matter of Examples 1-54 to optionally include wherein the stand count output module is configured to output the filtered measured values of crop width as a weed count.

Example 56 can include, or can optionally be combined with the subject matter of Examples 1-55 to optionally include wherein the stand count output module is configured to output the harvested standing crop value including a standing plant density.

Example 57 can include, or can optionally be combined with the subject matter of Examples 1-56 to optionally include a planting map module in communication with the reaping instrument controller, the planting map module includes a planting map of a crop, and the stand count output module is configured to associate the harvested standing crop value with the planting map and generate a consolidated planted and standing crop density map.

Example 58 can include, or can optionally be combined with the subject matter of Examples 1-57 to optionally include a yield monitor in communication with the reaping instrument controller, the yield monitor configured to measure a yield of the harvested standing crop, and wherein the reaping instrument controller includes a stand count yield module configured to identify yield per plant based on the measured yield and the harvested standing crop value.

Example 59 can include, or can optionally be combined with the subject matter of Examples 1-58 to optionally include a method for measuring reaping based yield comprising: measuring at least one crop characteristic of at least one crop including a stand characteristic with one or more reaping yield instruments associated with a harvester head; and generating a harvested standing crop value for the at least one crop based on at least the measured stand characteristic, generating including: counting the at least one crop as it is harvested based on the measured stand characteristic to determine a standing crop count, and comparing the measured stand characteristic against a filter threshold, and filtering the measured stand characteristic based on the comparison.

Example 60 can include, or can optionally be combined with the subject matter of Examples 1-59 to optionally include wherein counting the at least one crop includes counting standing stalks of the at least one crop.

Example 61 can include, or can optionally be combined with the subject matter of Examples 1-60 to optionally include wherein the one or more reaping yield instruments includes a beam emitter and a beam receiver, and counting the at least one crop includes interrupting a beam, the beam generated by a beam emitter at a first side of a section of a plurality of sections of the harvester head and received by a beam receiver at a second side of the section.

Example 62 can include, or can optionally be combined with the subject matter of Examples 1-61 to optionally include wherein the one or more reaping yield instruments includes a plurality of reaping yield instruments, and counting the at least one crop includes counting the at least one crop in each section of a plurality of sections with a respective reaping yield instrument of the plurality of reaping yield instruments.

Example 63 can include, or can optionally be combined with the subject matter of Examples 1-62 to optionally include wherein the stand characteristic includes a stalk width and the filter threshold includes a stalk width threshold, and comparing the measured stand characteristic includes comparing the measured stalk width against the stalk width threshold, and filtering the measured stalk width less than the stalk width threshold.

Example 64 can include, or can optionally be combined with the subject matter of Examples 1-63 to optionally include generating a weed count based on filtered stalk widths less than the stalk width threshold.

Example 65 can include, or can optionally be combined with the subject matter of Examples 1-64 to optionally include wherein generating the harvested standing crop value includes dividing the standing crop count by one or more of distance traveled or area covered by one or more sections of a plurality of sections of a harvester head to generate a standing crop count per unit of distance or per unit of area.

Example 66 can include, or can optionally be combined with the subject matter of Examples 1-65 to optionally include determining one or more of a volumetric or weight yield value of the at least one crop, and generating the harvested standing crop value for the at least one crop includes dividing one or more of the volumetric or weight yield value by the standing crop count, and the harvested standing crop value includes a volumetric or weight yield per plant value.

Example 67 can include, or can optionally be combined with the subject matter of Examples 1-66 to optionally include wherein generating the harvested standing crop value for the at least one crop includes: comparing the standing crop count against a planted crop count, and generating a crop density map based on the comparison of the standing crop count relative to the planted crop count.

Example 68 can include, or can optionally be combined with the subject matter of Examples 1-67 to optionally include wherein measuring the at least one crop characteristic and generating the harvested standing crop value includes: measuring the at least one crop characteristic of first and second crops including stand characteristics with one or more of the reaping yield instruments, and generating first and second harvested standing crop values for the respective first and second crops based on at least the measured stand characteristics.

Example 69 can include, or can optionally be combined with the subject matter of Examples 1-68 to optionally include wherein generating the first and second harvested standing crop values includes: counting the first crop as it is harvested based on the measured stand characteristic of the first crop to determine a first standing crop count, identifying a first crop density including comparing the first standing crop count to a first planted crop count, counting the second crop as it is harvested based on the measured stand characteristic of the second crop to determine a second standing crop count, and identifying a second crop density including comparing the second standing crop count to a second planted crop count.

Example 70 can include, or can optionally be combined with the subject matter of Examples 1-69 to optionally include wherein generating the first and second harvested standing crop values includes: counting the first crop as it is harvested based on the measured stand characteristic of the first crop to determine a first standing crop count, counting the second crop as it is harvested based on the measured stand characteristic of the second crop to determine a second standing crop count, determining first and second volumetric or weight yield values of each of the first and second crops, respectively, dividing one or more of the first volumetric or weight yield values by the first standing crop count and the first harvested standing crop value includes a first volumetric or weight yield per plant value, and dividing one or more of the second volumetric or weight yield values by the second standing crop count, and the second harvested standing crop value includes a second volumetric or weight yield per plant value.

Each of these non-limiting examples can stand on its own, or can be combined in any permutation or combination with any one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A reaping based yield monitor system comprising:
one or more reaping yield instruments configured for coupling with a harvester head, the one or more reaping yield instruments measure at least one crop characteristic of a harvested crop in each of a plurality of sections of the harvester head in an ongoing manner, the at least one crop characteristic measured in each of the plurality of sections having a proportion relative to the at least one crop characteristic measured in the plurality of sections; and
a yield monitor assembly in communication with the one or more reaping yield instruments, the yield monitor assembly includes:
a yield monitor with one or more yield instruments remotely positioned relative to the one or more reaping yield instruments, the yield monitor configured to determine a variable yield of the harvested crop in an ongoing manner, and
an apportionment module configured to allocate, in an ongoing manner, the variable yield of the harvested crop determined with the yield monitor to each of the sections of the harvester head according to the proportion of the at least one crop characteristic measured in each of the plurality of sections of the harvester head with the one or more reaping yield instruments.

2. The reaping based yield monitor system of claim 1, wherein the plurality of sections of the harvester head include a plurality of row sections of the harvester head.

3. The reaping based yield monitor system of claim 2, wherein the one or more reaping yield instruments includes a plurality of dedicated reaping yield instruments each configured for association with a respective row section of the plurality of row sections, and each of the dedicated reaping yield instruments is configured to measure the at least one crop characteristic at the associated respective row section.

4. The reaping based yield monitor system of claim 2, wherein the one or more reaping yield instruments includes a contact instrument at each of the plurality of row sections.

5. The reaping based yield monitor system of claim 1, wherein the one or more reaping yield instruments include one or more imaging instruments.

6. The reaping based yield monitor system of claim 5, wherein the one or more imaging instruments includes one or more of infrared (IR), optical, or video instruments.

7. The reaping based yield monitor system of claim 1 comprising the one or more yield instruments in communication with the yield monitor, the one or more yield instruments are different than the one or more reaping yield instruments,
the one or more yield instruments are configured to measure at least another crop characteristic the same as or different from the at least one crop characteristic, and
the yield monitor determines the variable yield of the harvested crop based on the measured at least another crop characteristic.

8. The reaping based yield monitor system of claim 7, wherein the one or more yield instruments are configured for coupling with a grain elevator of the harvester, and the one or more reaping yield instruments are configured for coupling with the harvester head upstream from the grain elevator and the one or more yield instruments.

9. The reaping based yield monitor system of claim 1, wherein the apportionment module includes a matching module configured to match the determined variable yield taken at a second time with at least one corresponding measurement of the at least one crop characteristic of the harvested crop measured with the one or more reaping yield instruments and taken at an earlier first time relative to the second time.

10. The reaping based yield monitor system of claim 1, wherein the one or more reaping yield instruments includes a plurality of reaping yield instruments, and the apportionment module includes:
a characteristic value module configured to store a plurality of ongoing consolidated values, each ongoing consolidated value corresponding to measurements of the crop characteristic measured with the plurality of reaping yield instruments taken at a first time for each of the plurality of sections of the harvester head,
a comparator configured to compare the determined variable yield against the plurality of ongoing consolidated values, the determined variable yield determined at a second later time relative to the first time,
a matching module configured to match the determined variable yield with an ongoing consolidated value of the plurality of ongoing consolidated values based on the comparison, and
an assignment module configured to divide the matched determined variable yield into variable yield portions between each section of the plurality of sections of the harvester head according to the measurements of the at least one crop characteristic measured with the plurality of reaping yield instruments.

11. The reaping based yield monitor system of claim 10, wherein the apportionment module includes a delay module configured to measure a delay time between the first and second times of the measurements of the crop characteristics and the determined variable yield.

12. The reaping based yield monitor system of claim 10, wherein the apportionment module includes an indexing module in communication with a field map, and the indexing module is configured to map the variable yield portions of each of the plurality of sections to portions of the field map corresponding to each of the harvester head sections at the first time.

13. The reaping based yield monitor system of claim 12, wherein the sections of the harvester head include row sections of the harvester head, and the portions of the field map include crop rows, and
the indexing module is configured to map the variable yield portions of each of the plurality of row sections to the crop rows of the field map corresponding to each of the harvester head row sections at the first time.

14. The reaping based yield monitor system of claim 1, wherein the one or more reaping yield instruments includes a contact instrument coupled along at least one deck plate of a harvester row section.

15. The reaping based yield monitor system of claim 14, wherein the contact instrument includes a load cell system.

16. The reaping based yield monitor system of claim 15, wherein the contact instrument includes a protective plate covering the load cell system.

17. The reaping based yield monitor system of claim 1, wherein the one or more reaping yield instruments includes a plurality of reaping yield instruments, and the apportionment module includes:
a matching module configured to match the determined variable yield with measurements of the at least one crop characteristic in each of the plurality of sections of the harvester head according to a delay time between the measuring of the at least one crop characteristic and determining of the variable yield, and
an assignment module configured to divide the matched determined variable yield into variable yield portions between each of the sections of the plurality of sections according to the measurements of the at least one crop characteristic in each of the plurality of sections with the plurality of reaping yield instruments.

18. A reaping based yield measuring system comprising:
one or more reaping yield instruments configured for coupling with a harvester head, the one or more reaping yield instruments measure at least one crop characteristic in each of a plurality of sections of the harvester head in an ongoing manner, the at least one crop characteristic measured in each of the plurality of sections having a proportion relative to the at least one crop characteristic measured in the plurality of sections;
a reaping instrument controller in communication with the one or more reaping yield instruments, the reaping instrument controller configured for communication with a yield monitor having one or more yield instruments different from the one or more reaping yield instruments; and
wherein the reaping instrument controller is configured to allocate, in an ongoing manner, an ongoing determined variable yield of harvested crop generated by the yield monitor with the one or more yield instruments to each of the sections of the plurality of sections according to the proportions of the at least one crop characteristic in each of the plurality of sections of the harvester head.

19. The reaping based yield measuring system of claim 18 comprising the yield monitor in communication with the reaping instrument controller, the yield monitor is configured to determine the variable yield of the harvested crop.

20. The reaping based yield measuring system of claim 19 comprising the one or more yield instruments in communication with the yield monitor, the one or more yield instruments are configured to measure at least another crop characteristic the same as or different from the at least one crop characteristic, and the yield monitor determines the variable yield of the harvested crop based on the measured at least another crop characteristic measured by the one or more yield instruments.

21. The reaping based yield measuring system of claim 20, wherein the one or more yield instruments are configured for coupling with a grain elevator of the harvester, and the one or more reaping yield instruments are configured for coupling with the harvester head upstream from the grain elevator and the one or more yield instruments.

22. The reaping based yield measuring system of claim 18, wherein the plurality of sections of the harvester head include a plurality of row sections of the harvester head.

23. The reaping based yield measuring system of claim 22, wherein the one or more reaping yield instruments includes a plurality of dedicated reaping yield instruments each configured for association with corresponding row sections of the plurality of row sections, and each of the dedicated reaping yield instruments is configured to measure the at least one crop characteristic at the respective corresponding row section.

24. The reaping based yield measuring system of claim 22, wherein the one or more reaping yield instruments includes a contact instrument configured for positioning at each row section of the plurality of row sections.

25. The reaping based yield measuring system of claim 18, wherein the one or more reaping yield instruments include one or more imaging instruments.

26. The reaping based yield measuring system of claim 25, wherein the one or more imaging sensors includes one or more of infrared (IR), optical, or video instruments.

27. The reaping based yield measuring system of claim 25, wherein
the one or more imaging instruments includes a plurality of dedicated imaging instruments each configured for association with respective sections of the plurality of sections of the harvester head to measure the at least one crop characteristic at each of the sections.

28. The reaping based yield measuring system of claim 25, wherein the one or more imaging instruments includes a single stream video instrument configured to measure the at least one crop characteristic at each section of the plurality of sections.

29. The reaping based yield measuring system of claim 18, wherein the one or more reaping yield instruments include a plurality of reaping yield instruments, and the reaping instrument controller includes:
a characteristic value module configured to store a plurality of ongoing consolidated values, each ongoing consolidated value corresponding to measurements of the crop characteristic measured with the plurality of reaping yield instruments taken at a first time for each of the plurality of sections of the harvester head,
a comparator configured to compare the determined variable yield against the plurality of ongoing consolidated values, the determined variable yield determined at a second later time relative to the first time,
a matching module configured to match the determined variable yield with an ongoing consolidated value of the plurality of ongoing consolidated values based on the comparison, and
an assignment module configured to divide the determined variable yield into variable yield portions between each section of the plurality of sections of the harvester head according to the measurements of the at least one crop characteristic measured with the plurality of reaping yield instruments.

30. The reaping based yield monitor system of claim 29, wherein the reaping instrument controller includes a delay module configured to measure a delay time between the first and second times of the measurements of the crop characteristics and the determined variable yield.

31. The reaping based yield monitor system of claim 29, wherein the reaping instrument controller includes an indexing module in communication with a field map, and
the indexing module is configured to map the variable yield portions of each of the plurality of sections to portions of the field map corresponding to each of the harvester head sections at the first time.

32. The reaping based yield measuring system of claim 30, wherein the sections of the harvester head include row sections of the harvester head, and the portions of the field include crop rows, and
the indexing module is configured to associate the apportioned variable yield of the harvested crop at each of the row sections of the harvester head to the portions of crop rows of the field on a field map corresponding to each location of the row sections of the harvester head based on the delay time.

33. The reaping based yield measuring system of claim 18, wherein the one or more reaping yield instruments includes a contact instrument coupled along at least one deck plate of a harvester row section.

34. The reaping based yield measuring system of claim 33, wherein the contact instrument includes a load cell system.

35. The reaping based yield measuring system of claim 34, wherein the contact instrument includes a protective plate covering the load cell system.

36. The reaping based yield monitor system of claim 18, wherein the reaping instrument controller includes:
a matching module configured to match the determined variable yield with measurements of the at least one crop characteristic in each of the plurality of sections of the harvester head according to a delay time between the measuring of the at least one crop characteristic and determining of the variable yield, and
an assignment module is configured to divide the matched determined variable yield into variable yield portions between each of the sections of the plurality of sections according to the measurements of the at least one crop characteristic in each of the plurality of sections with the plurality of reaping yield instruments.

* * * * *